(12) United States Patent
Albrecht et al.

(10) Patent No.: US 9,856,270 B2
(45) Date of Patent: Jan. 2, 2018

(54) DOLUTEGRAVIR SALTS

(71) Applicant: Ratiopharm GmbH, Ulm (DE)

(72) Inventors: Wolfgang Albrecht, Ulm (DE); Ludovic Coutable, Ulm (DE); Gertraud Koellner, Neu-Ulm (DE)

(73) Assignee: Ratiopharm GMBH, Ulm (DE)

( * ) Notice: Subject to any disclaimer, the term of this patent is extended or adjusted under 35 U.S.C. 154(b) by 0 days.

(21) Appl. No.: 14/905,062

(22) PCT Filed: Jul. 17, 2014

(86) PCT No.: PCT/US2014/047022
§ 371 (c)(1),
(2) Date: Jan. 14, 2016

(87) PCT Pub. No.: WO2015/009927
PCT Pub. Date: Jan. 22, 2015

(65) Prior Publication Data
US 2016/0145269 A1 May 26, 2016

Related U.S. Application Data

(60) Provisional application No. 61/847,430, filed on Jul. 17, 2013, provisional application No. 61/941,079, filed on Feb. 18, 2014.

(51) Int. Cl.
*C07D 498/14* (2006.01)

(52) U.S. Cl.
CPC ........ *C07D 498/14* (2013.01); *C07B 2200/13* (2013.01)

(58) Field of Classification Search
CPC .................................................. C07D 498/14
USPC .......................................... 544/95; 514/230.2
See application file for complete search history.

(56) References Cited

U.S. PATENT DOCUMENTS

| | | |
|---|---|---|
| 2006/0122205 A1 | 6/2006 | Belyk |
| 2006/0211687 A1* | 9/2006 | Palucki ............... C07D 471/04 514/222.2 |
| 2012/0022251 A1 | 1/2012 | Sumino |

FOREIGN PATENT DOCUMENTS

| | | | | |
|---|---|---|---|---|
| JP | WO 2006116764 A1 * | 11/2006 | .......... | C07D 471/04 |
| WO | 2004080402 | 9/2004 | | |
| WO | WO 2004080402 A2 * | 9/2004 | .......... | C07D 471/04 |
| WO | 2006116764 | 11/2006 | | |
| WO | WO 2010011812 A1 * | 1/2010 | .......... | A61K 31/535 |
| WO | 2010068253 | 6/2010 | | |
| WO | 2013038407 | 3/2013 | | |
| WO | 2014125124 | 8/2014 | | |

OTHER PUBLICATIONS

Stahl et al., eds., Handbook of pharmaceutical salts. Properties, selection and use (Wiley-VCH, 2008), pp. 265-327.*
International Preliminary Report on Patentability and Written Opinion for International Application No. PCT/US2014/047022 dated Jan. 19, 2016.
International Search Report for International Application No. PCT/US2014/047022 dated Sep. 24, 2014.
Written Opinion of the International Searching Authority for International Application No. PCT/US2014/047022 dated Sep. 24, 2014.

* cited by examiner

*Primary Examiner* — Kahsay Habte
(74) *Attorney, Agent, or Firm* — Gary J. Gershik; Cooper & Dunham LLP

(57) ABSTRACT

Dolutegravir potassium salt and solid state forms thereof are provided, as well as methods of making and interconverting these forms. The Dolutegravir potassium forms, and pharmaceutical compositions containing them, may be used to treat subjects in need of medical treatment, such as for HIV infection.

30 Claims, 29 Drawing Sheets

DOLUTEGRAVIR SALTS

CROSS REFERENCE TO RELATED APPLICATIONS

This application is the National Phase filing of International Application Number PCT/US2014/047022, filed 17 Jul. 2014, and claims priority to U.S. provisional patent Application No. 61/847,430, filed 17 Jul. 2013, and to U.S. provisional patent Application No. 61/941,079, filed 18 Feb. 2014, the entire contents of which applications are incorporated herein by reference for all purposes.

FIELD OF THE INVENTION

The present invention relates to Dolutegravir potassium salt, solid state forms thereof, processes for preparation thereof and pharmaceutical compositions thereof.

BACKGROUND OF THE INVENTION

Dolutegravir, also referred to as Dolutegravir free-acid, has the chemical name (4R,12aS)-N-(2,4-difluorobenzyl)-7-hydroxy-4-methyl-6,8-dioxo-3,4,6,8,12,12a-hexahydro-2H-pyrido[1',2':4,5]pyrazino[2,1-b][1,3]oxazine-9-carboxamide. Dolutegravir has the following chemical structure:

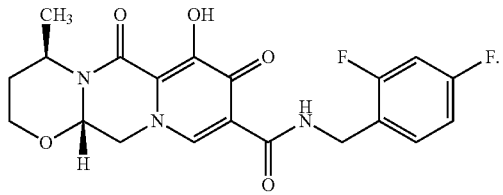 [SMILES: C[C@@H]1CCO[C@H]2Cn3cc(C(=O)NCc4ccc(F)cc4F)c(=O)c(O)c3C(=O)N12]

Dolutegravir is known from WO2006/116764 as a compound possessing antiviral activity, in particular an inhibitory activity against HIV integrase.

A sodium salt of Dolutegravir and a crystalline form of this sodium salt or a hydrate thereof are disclosed in WO2010/068253.

Dolutegravir is marketed as TIVICAY by GlaxoSmithKline. TIVICAY is a human immunodeficiency virus type 1 (HIV-1) integrase strand transfer inhibitor (INSTI) indicated in combination with other antiretroviral agents for the treatment of HIV-1 infection.

Polymorphism, the occurrence of different crystal forms, is a property of some molecules and molecular complexes. A single compound, like Dolutegravir, may give rise to a variety of polymorphs having distinct crystal structures and physical properties like melting point, thermal behaviors (e.g. measured by thermogravimetric analysis—"TGA", or differential scanning calorimetry—"DSC"), powder X-ray diffraction (PXRD) pattern, infrared absorption fingerprint, Raman absorption fingerprint, and solid state ($^{13}$C—) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, improving the dissolution profile, or improving stability (polymorph as well as chemical stability) and shelf-life. These variations in the properties of different salts and solid state forms may also provide improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to use variations in the properties and characteristics of a solid active pharmaceutical ingredient for providing an improved product.

Discovering new salts, solid state forms and solvates of a pharmaceutical product can provide materials having desirable processing properties, such as ease of handling, ease of processing, storage stability, and ease of purification or as desirable intermediate crystal forms that facilitate conversion to other salts or polymorphic forms. New salts, polymorphic forms and solvates of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life. For at least these reasons, there is a need for additional salts and solid state forms (including solvated forms) of Dolutegravir.

SUMMARY OF THE INVENTION

The present invention relates to Dolutegravir potassium salt, to solid state forms thereof, to processes for preparation thereof, and to pharmaceutical compositions comprising at least one, or a combination of the solid state forms of the potassium salt. Accordingly, the present invention provides amorphous as well as crystalline forms of Dolutegravir potassium salt.

The present invention also provides the use of the solid state forms of Dolutegravir potassium salt for preparing Dolutegravir or other Dolutegravir salts, and solid state forms thereof.

In another embodiment, the present invention encompasses the above described solid state forms of Dolutegravir potassium salt for use in the preparation of pharmaceutical compositions, preferably for the treatment of HIV infection.

The present invention further provides pharmaceutical formulations comprising any one of, or a mixture of the solid state forms of Dolutegravir potassium salt according to the present invention.

The present invention encompasses processes to prepare said pharmaceutical formulations of Dolutegravir potassium salt comprising combining any one or a mixture of the above solid state forms and at least one pharmaceutically acceptable excipient.

In another embodiment the present invention encompasses the use of the above described solid state forms of Dolutegravir potassium salt for the preparation of pharmaceutical compositions.

The solid state forms as defined herein as well as the pharmaceutical compositions and the pharmaceutical formulations of Dolutegravir potassium salt can be used as medicaments, particularly for the treatment of HIV infection.

The present invention also provides a method of treating HIV infection, comprising administering a therapeutically effective amount of the Dolutegravir potassium salt and solid state forms thereof of the present invention, or at least one of the above pharmaceutical compositions or formulations, to a subject suffering from HIV infection, or otherwise in need of the treatment.

The present invention also provides the use of Dolutegravir potassium salt and solid state forms thereof of the present invention, or at least one of the above pharmaceutical compositions or formulations for the manufacture of a medicament for treating HIV infection.

DETAILED DESCRIPTION OF THE INVENTION

Figure 1:
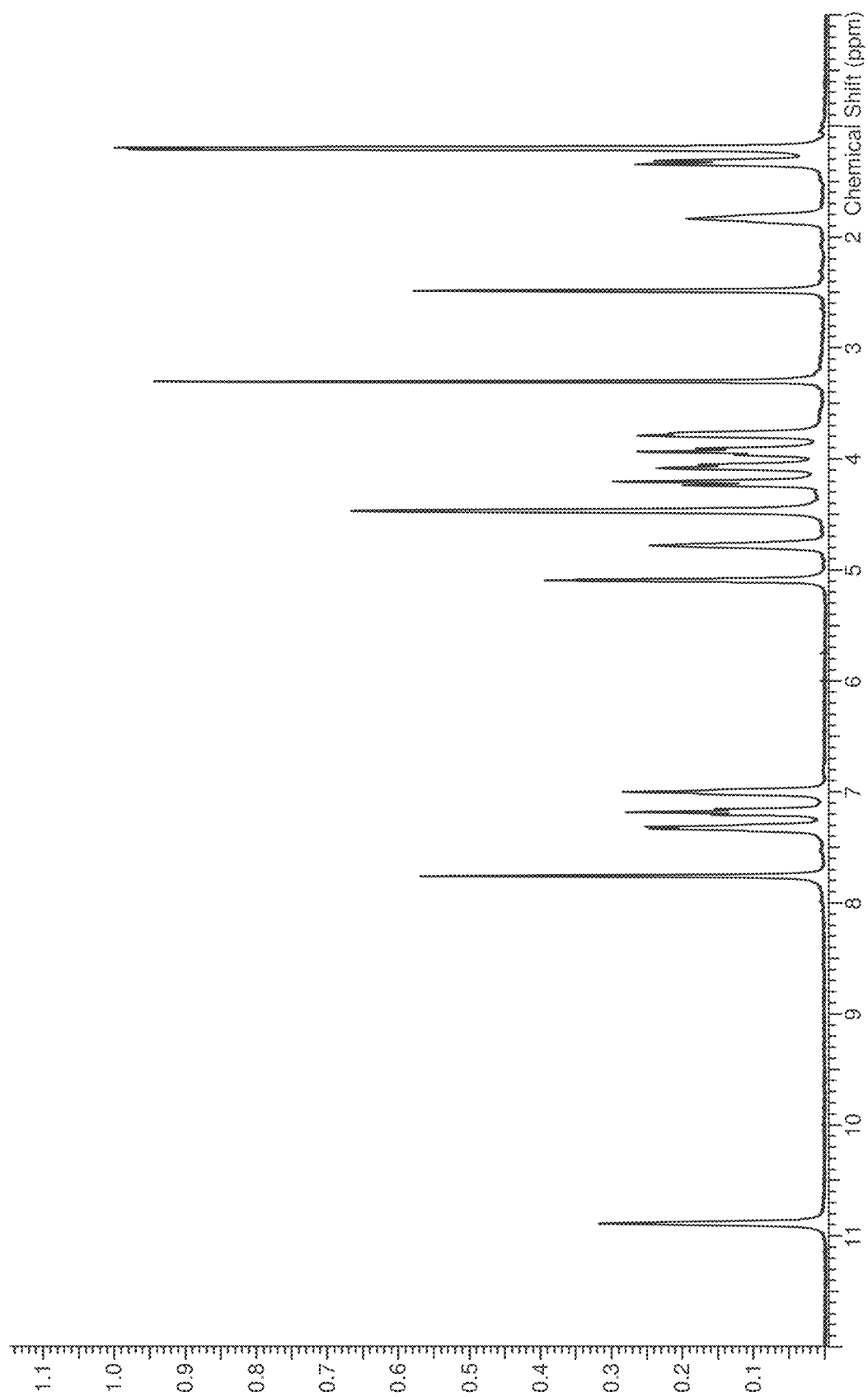
FIG. 1 shows a $^1$H-NMR spectrum for Dolutegravir potassium salt.

The present invention relates to Dolutegravir potassium salt, to solid state forms thereof, to processes for preparation thereof and to pharmaceutical compositions comprising Dolutegravir potassium salt. Accordingly, the present invention provides amorphous as well as crystalline forms of this salt. The invention also relates to the conversion of the Dolutegravir potassium salt and its solid state forms to Dolutegravir or other Dolutegravir salts.

Depending on which other salts or solid state forms comparison is made with, the salt and solid state forms of the present invention may have advantageous properties selected from at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, or bulk density A crystal form may be referred to herein as being characterized by graphical data "as depicted in" a Figure. Such data include, for example, powder X-ray diffractograms and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Dolutegravir salt referred to herein as being characterized by graphical data "as depicted in" a Figure will thus be understood to include any crystal forms of the Dolutegravir salt characterized with the graphical data having such small variations, as are well known to the skilled person, in comparison with the Figure.

A solid state form (or polymorph) may be referred to herein as polymorphically pure or as substantially free of any other solid state (or polymorphic) forms. As used herein in this context, the expression "substantially free of any other forms" will be understood to mean that the solid state form contains 20% or less, 10% or less, 5% or less, 2% or less, or 1% or less of any other forms of the subject compound as measured, for example, by XRPD. Thus, a solid state form of Dolutegravir described herein as being substantially free of any other solid state forms would be understood to contain greater than 80% (w/w), greater than 90% (w/w), greater than 95% (w/w), greater than 98% (w/w), or greater than 99% (w/w) of the subject solid state form of Dolutegravir. Accordingly, in some embodiments of the invention, the described solid state forms of Dolutegravir may contain from 1% to 20% (w/w), from 5% to 20% (w/w), or from 5% to 10% (w/w) of one or more other solid state forms of Dolutegravir. Thus, preferably, as used herein, the expression "substantially free of any other forms" will be understood to mean that the solid state form of Dolutegravir potassium contains 20% or less, 10% or less, 5% or less, 2% or less, or 1% or less of any other forms of Dolutegravir potassium as measured, for example, by XRPD. Thus, solid state form of Dolutegravir potassium as described herein as being substantially free of any other solid state forms would be understood to contain greater than 80% (w/w), greater than 90% (w/w), greater than 95% (w/w), greater than 98% (w/w), or greater than 99% (w/w) of the subject solid state form of Dolutegravir potassium. Accordingly, in some embodiments of the invention, the described solid state forms of Dolutegravir potassium may contain from 1% to 20% (w/w), from 5% to 20% (w/w), or from 5% to 10% (w/w) of one or more other solid state forms of Dolutegravir potassium.

As used herein, the term "Dolutegravir-K" refers to Dolutegravir potassium salt.

As used herein, unless stated otherwise, PXRD peaks reported herein are preferably measured using $CuK_\alpha$ radiation, $\lambda=1.5418$ Å.

As used herein, the term "isolated" in reference to Dolutegravir salt or solid state forms thereof of the present invention corresponds to Dolutegravir salt or solid state form thereof that is physically separated from the reaction mixture in which it is formed.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, typically about 16 hours. Thus, preferably, the term "overnight" refers to a time period of about 12 to about 18 hours, about 14 to about 18 hours and especially about 16 hours.

As used herein, the expression "wet crystalline form" refers to a polymorph that was not dried using any conventional techniques to remove residual solvent. Examples for such conventional techniques can be, but not limited to, evaporation, vacuum drying, oven drying, drying under nitrogen flow, etc.

As used herein, the expression "dry crystalline form" refers to a polymorph that was dried using any conventional techniques to remove residual solvent. Examples of such conventional techniques can be, but are not limited to, evaporation, vacuum drying, oven drying, drying under nitrogen flow, etc.

As used herein, and unless stated otherwise, the term "anhydrous" in relation to crystalline Dolutegravir relates to a crystalline Dolutegravir which does not include any crystalline water (or other solvents) in a defined, stoichiometric amount within the crystal. Moreover, an "anhydrous" form does not contain more than 1% (w/w) of either water or organic solvents as measured for example by TGA.

The term "solvate", as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

The amount of solvent employed in a chemical process, e.g., a reaction or a crystallization may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding MTBE (1.5 v/v) to a 100 ml reaction mixture would indicate that 150 mL of MTBE was added.

As used herein the term non-hygroscopic in relation to crystalline Dolutegravir of the present invention refers to less than 3%, or less than 2%, or for example less than 1% (w/w) absorption of water at 25° C. and 75% RH, by the crystalline Dolutegravir as determined for example by TGA or DVS. Water can be for example atmospheric water. Preferably, as used herein the term non-hygroscopic in relation to crystalline Dolutegravir potassium refers to less than 3%, or less than 2%, or for example less than 1% (w/w) adsorption of water upon exposure to a temperature of 25° C. and 75% RH for about 24 hours and preferably 48 hours by the crystalline Dolutegravir potassium, as determined for example by TGA. Water can be for example atmospheric water.

As used herein the term non hygroscopic in relation to amorphous Dolutegravir forms refers to adsorption of less 5% e.g. less than 4% of water as measured for example by dynamic vapour sorption (DVS) experiment during exposure for about 40 to about 60 hours e.g. for 48 hours to 75% relative humidity at 25° C. Furthermore, water may be reversibly adsorbed on the surface without any impact on the solid-state characteristics of amorphous Dolutegravir potassium.

As used herein, the term "reduced pressure" refers to a pressure of about 10 mbar to about 50 mbar.

As used herein, and unless indicated otherwise, the term "thermo-dynamical stability" in relation to Dolutegravir salt (preferably Dolutegravir potassium) or a solid state form thereof refers to resistance of the solid state form to polymorphic conversion under certain conditions, for example, heating. In some embodiments, the term refers to less than 20%, 10%, 5%, 1%, or 0.5% (w/w) conversion of crystalline Dolutegravir or a Dolutegravir salt form (preferably Dolutegravir potassium) to any other solid state form of Dolutegravir or a Dolutegravir salt (preferably Dolutegravir potassium) as measured by XRPD. In some embodiments, the conversion is 1%-20%, 1%-10% or 1%-5% (w/w). Alternatively, the term "thermo-dynamical stability" refers to at least 80%, 90%, 95%, 99% or 99.5% (w/w) of the original form is still present under the testing conditions as determined, for example, by XRPD.

As used herein crystalline Form I of Dolutegravir free acid refers to a crystalline form which may be characterized by data selected from one or more of the following: PXRD pattern having characteristic diffraction peaks at 5.4°±0.2°, 10.7°±0.2°, 12.3°±0.2°, 15.2°±0.2°, and 16.4°±0.2° two theta; infrared absorption spectra having characteristic peaks at 1658 cm$^{-1}$±2 cm$^{-1}$, 1628 cm$^{-1}$+2 cm$^{-1}$, 1540 cm$^{-1}$±2 cm$^{-1}$ and 1498 cm$^{-1}$±±2 cm$^{-1}$ and combinations of these data.

The present invention encompasses Dolutegravir potassium salt. The Dolutegravir potassium salt can be characterized by a $^1$H-NMR spectrum substantially as shown in FIG. 1. The Dolutegravir potassium salt can be solid, Dolutegravir potassium salt may be in crystalline or amorphous form. Preferably the Dolutegravir potassium salt is solid crystalline.

As mentioned above, Dolutegravir potassium has advantageous properties. For example, improved dissolution, compared to the sodium salt, under certain conditions as depicted in Example 9.

Figure 24:
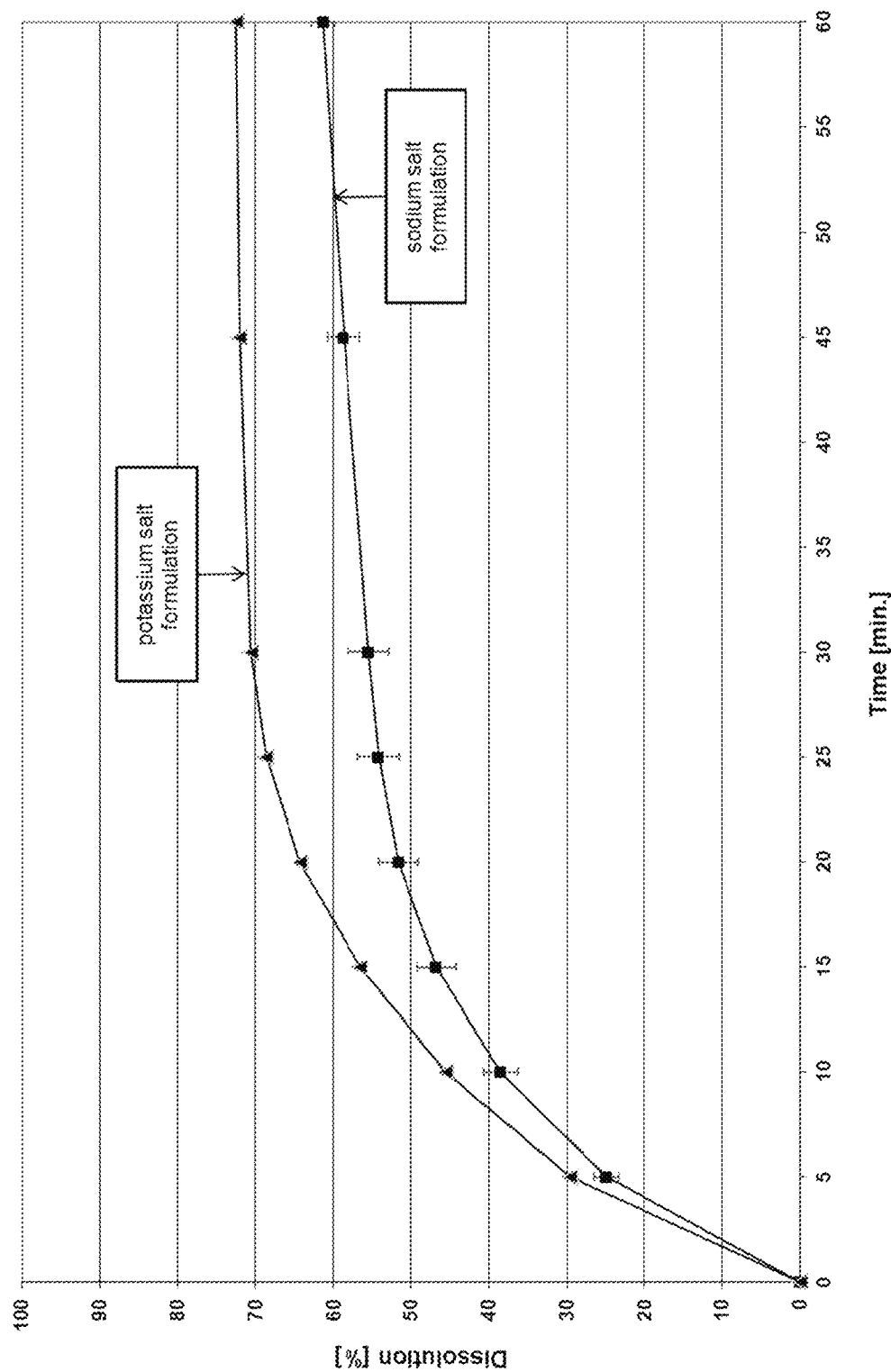
FIG. 24 shows a plot comparing the percent dissolution of Dolutegravir over time for: potassium salt formulation and sodium salt formulation.

In particular, Dolutegravir potassium salt may provide a relatively improved dissolution rate, e.g., a faster and/or higher dissolution rate of a pharmaceutical composition comprising it compared to the sodium salt as depicted in FIG. 24.

Figure 2:
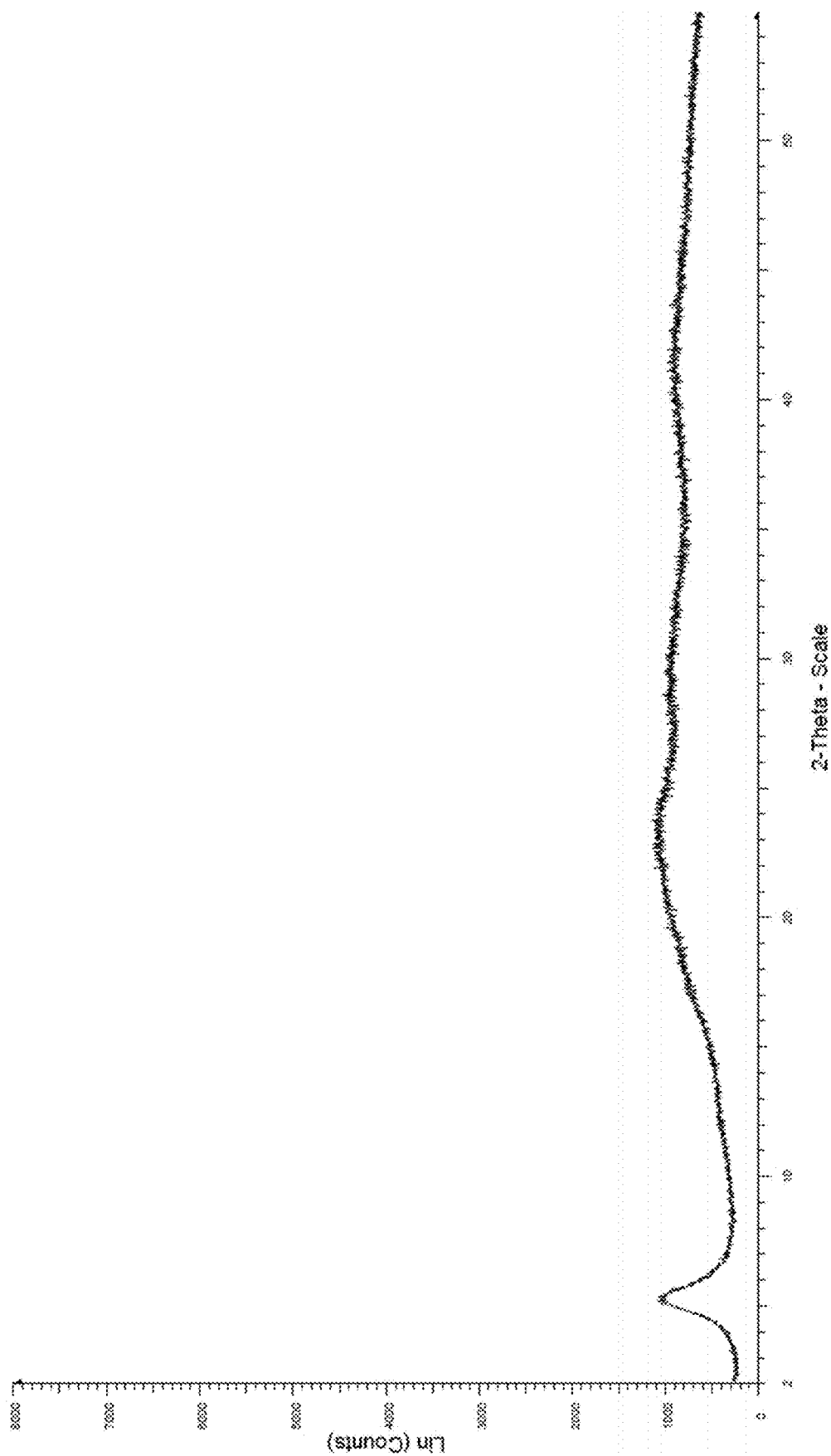
FIG. 2 shows an X-ray powder diffraction pattern ("powder XRD" or "PXRD") for amorphous Dolutegravir potassium.

The present invention comprises an amorphous form of Dolutegravir potassium salt. The amorphous form of Dolutegravir potassium salt can be characterized by an X-ray powder diffraction pattern as depicted in FIG. 2.

Amorphous Dolutegravir potassium salt may be further characterized by a DSC thermogram showing a very broad endotherm between about 40° C. to about 130° C. (±2° C.), a very small exotherm between 250° C. and 257° C. (±2° C.), a broad endotherm between 290° C. and 330° C. (±2° C.), followed by a broad exotherm, which corresponds to decomposition of the sample.

Figure 3:
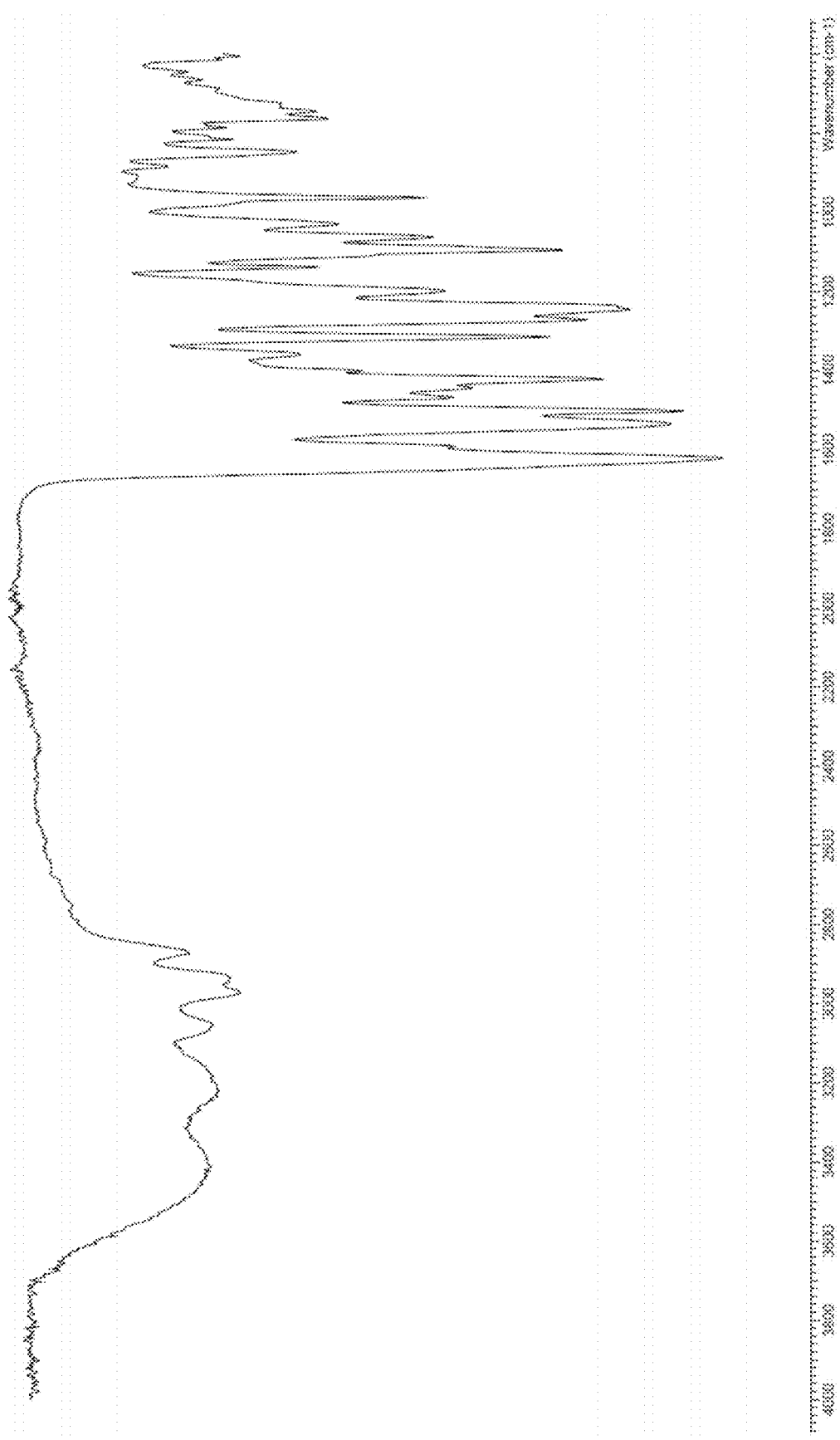
FIG. 3 shows an IR spectrum for amorphous Dolutegravir potassium salt.
Figure 23:
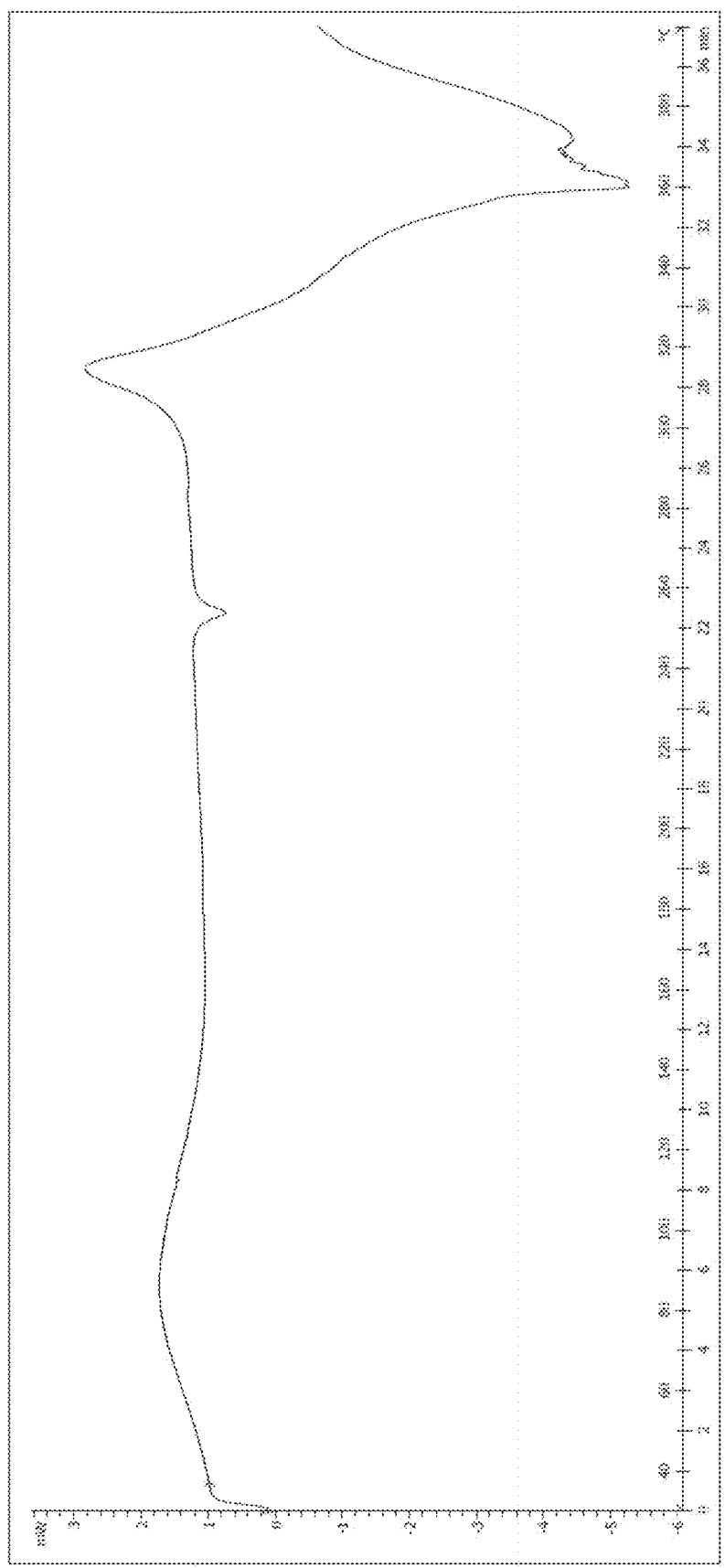
FIG. 23 shows a DSC thermogram for amorphous Dolutegravir potassium salt.

Amorphous form of Dolutegravir potassium salt can be further characterized by an FTIR spectrum as depicted in FIG. 3; a DSC thermogram as depicted in FIG. 23 and combinations of these data.

As mentioned above, the amorphous form of Dolutegravir potassium salt has advantageous properties. For example, the amorphous form of Dolutegravir potassium salt may have polymorphic stability. Thus, for example, preferably the amorphous Dolutegravir potassium salt contains less than 20%, less than 10%, less than 5%, 1%, or less 0.5% by weight of any crystalline form of Dolutegravir potassium as measured by XRPD. In some embodiments, the conversion is 1%-20%, 1%-10% or 1%-5% (w/w) following storage at 40° C., and 75% RH for 12 weeks.

In particular, the amorphous form of Dolutegravir potassium salt may be stable for at least 12 weeks under storage condition of 40° C./75% RH. Preferably, following storage under these conditions, the amorphous Dolutegravir potassium salt contains less than 20%, less than 10%, less than 5%, 1%, or less 0.5% by weight of any crystalline form of Dolutegravir potassium as determined by XRPD.

Moreover, the amorphous potassium salt may be non hygroscopic. Preferably, the amorphous Dolutegravir potassium absorbs less than 5%, or less than 4% by weight of water following exposure to 75% relative humidity at 25° C. for about 40 to about 60 hours, and preferably for 48 hours.

Figure 4:
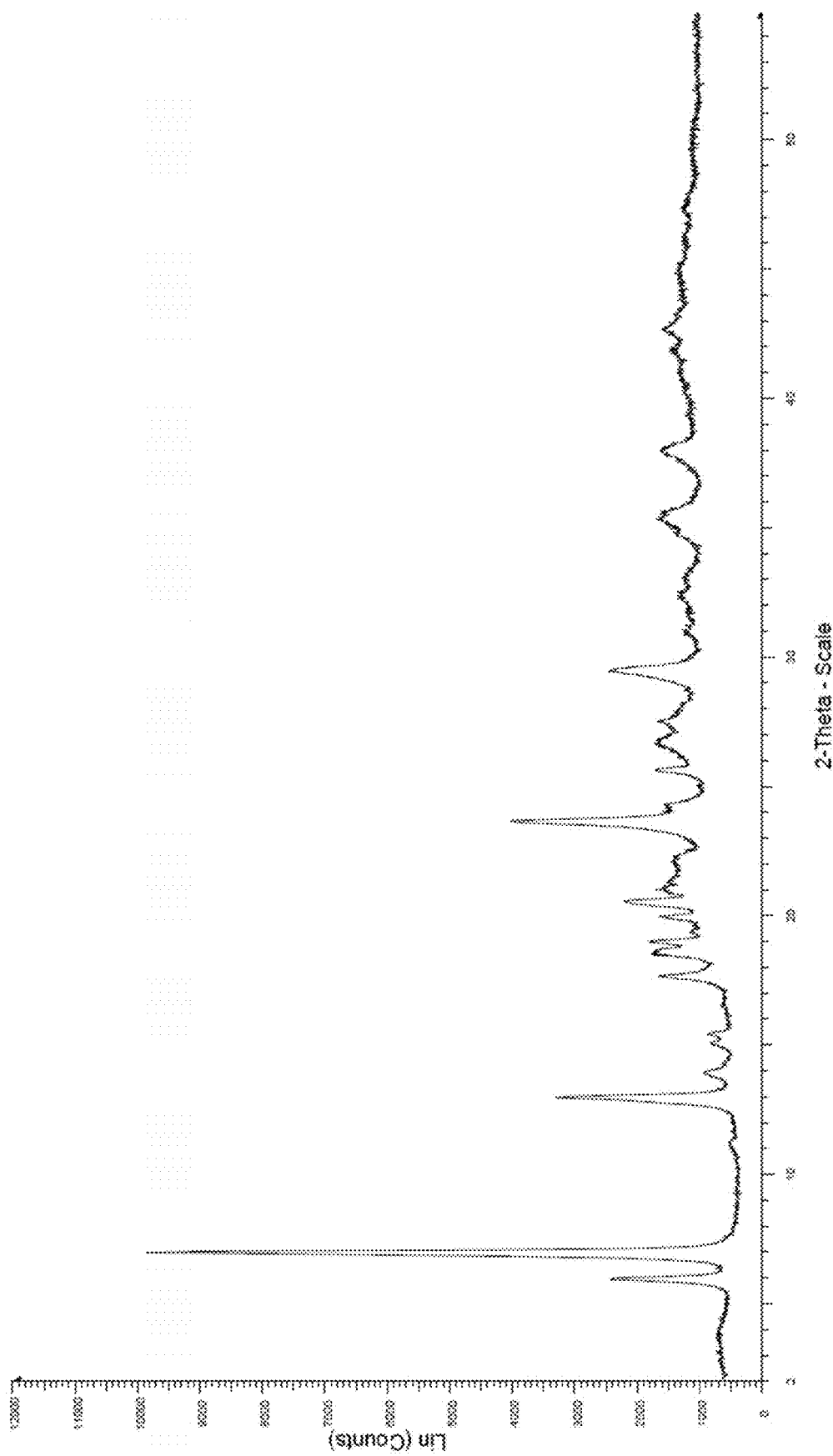
FIG. 4 shows a powder XRD for crystalline Dolutegravir potassium form II.
Figure 4A:
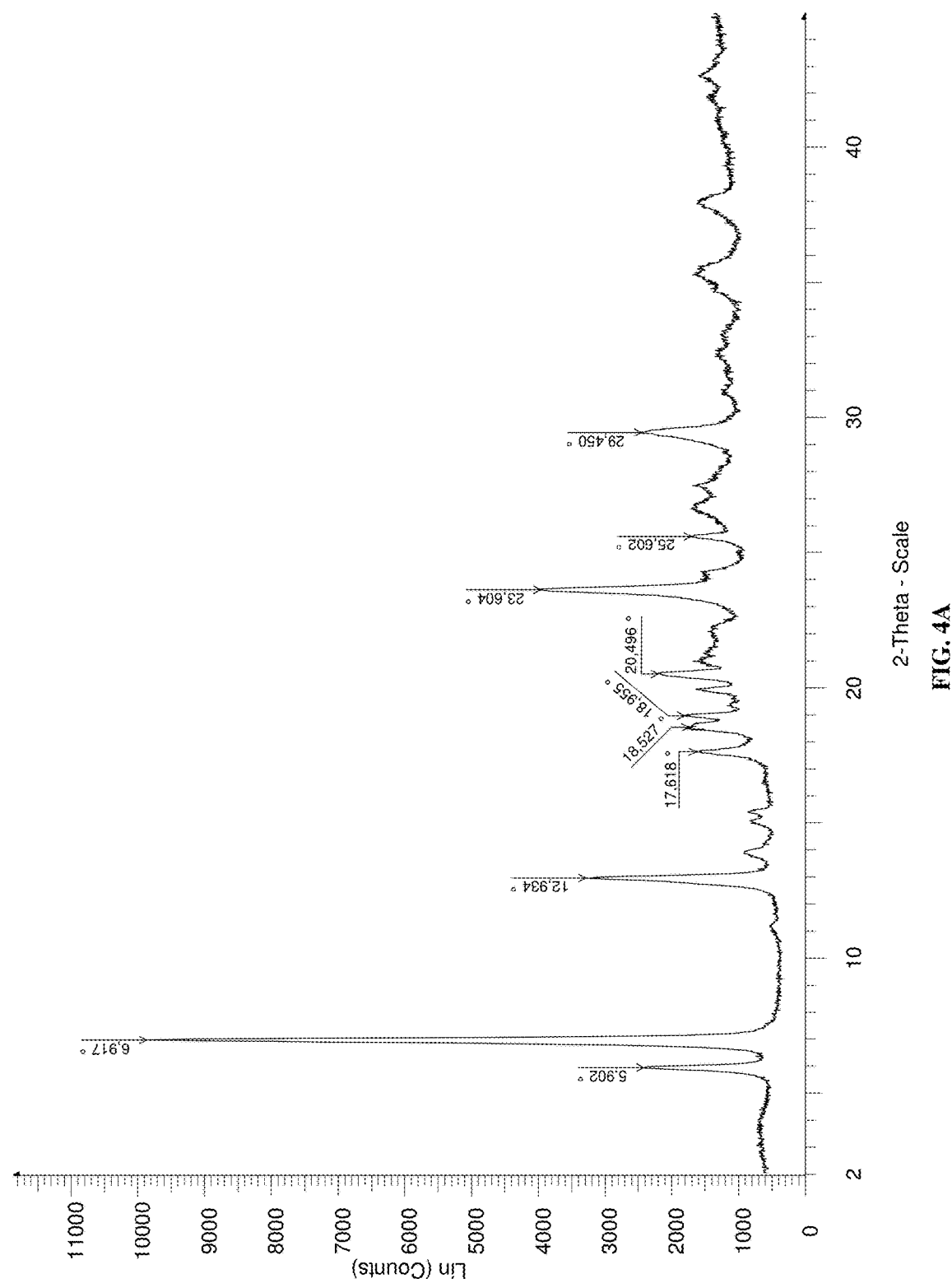
FIG. 4A shows a powder XRD for crystalline Dolutegravir potassium form II.

The present invention further encompasses a crystalline form of Dolutegravir potassium salt, designated as Form II, characterized by data selected from one or more of the following: a PXRD pattern having peaks at 5.90, 6.92, 12.9, 23.6 and 29.5 degrees 2-theta±0.2 degrees 2-theta; a PXRD pattern as depicted in FIG. 4; and combinations of these data.

Crystalline Form II of Dolutegravir potassium salt may be further characterized by a DSC thermogram showing a very broad endotherm at about 66° C. to about 133° C. (±2° C.), a large, broad exotherm at about 300° C. to about 330° C. (±2° C.), and finally an endotherm with a peak temperature of about 331° C. (±0.5° C.).

Figure 5:
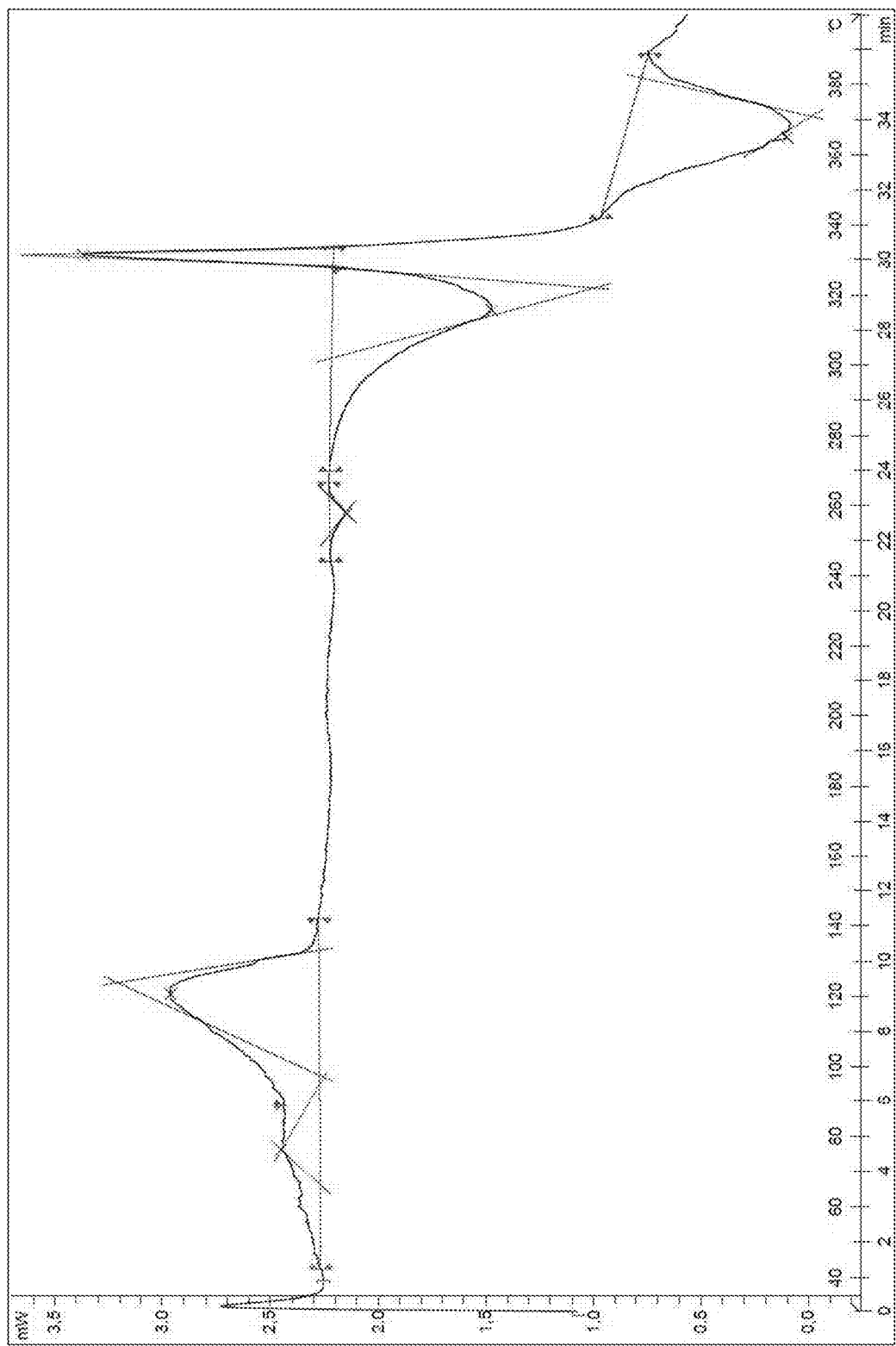
FIG. 5 shows a DSC thermogram for crystalline Dolutegravir potassium form II.
Figure 15:
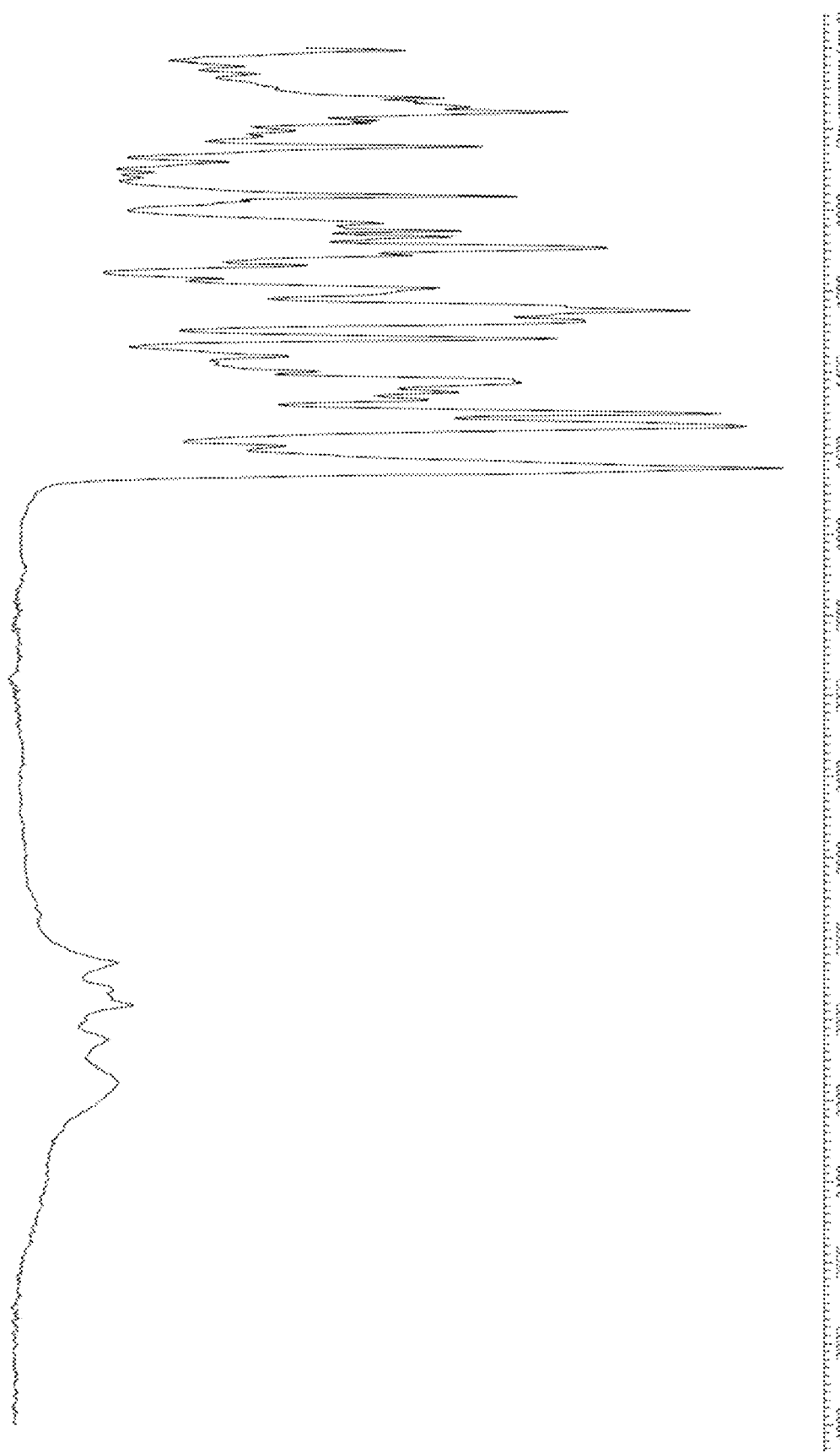
FIG. 15 shows an IR spectrum for Dolutegravir potassium Form II.

Crystalline Form II of Dolutegravir potassium salt may be further characterized by data selected from one or more of the following: a PXRD pattern having peaks at 5.90, 6.92, 12.9, 23.6 and 29.5 degrees 2-theta±0.2 degrees 2-theta, and also having one, two, three, four or five additional peaks selected from 17.6, 18.5, 19.0, 20.5 and 25.6 degrees two theta±0.2 degrees two theta; a DSC thermogram as depicted in FIG. 5; an FTIR spectrum as depicted in FIG. 15; and combinations of these data.

Alternatively, crystalline Form II of Dolutegravir potassium salt may be further characterized by data selected from one or more of the following: a PXRD pattern having peaks at 5.9, 6.9, 12.9, 23.6 and 29.5 degrees 2-theta±0.2 degrees 2-theta, and also having one, two, three, four or five additional peaks selected from 17.6, 18.5, 19.0, 20.5 and 25.6 degrees two theta±0.2 degrees two theta; a DSC thermogram as depicted in FIG. 5; an FTIR spectrum as depicted in FIG. 15; and combinations of these data.

Crystalline Form II of Dolutegravir potassium salt may be characterized by each of the above characteristics alone and/or by all possible combinations, e.g. by an X-ray powder diffraction pattern having peaks at 5.90, 6.92, 12.9, 23.6 and 29.5 degrees two theta±0.2 degrees two theta and an X-ray powder diffraction pattern as depicted in FIG. 4. Preferably, crystalline Form II is an ethanol solvate of Dolutegravir potassium.

Figure 6:
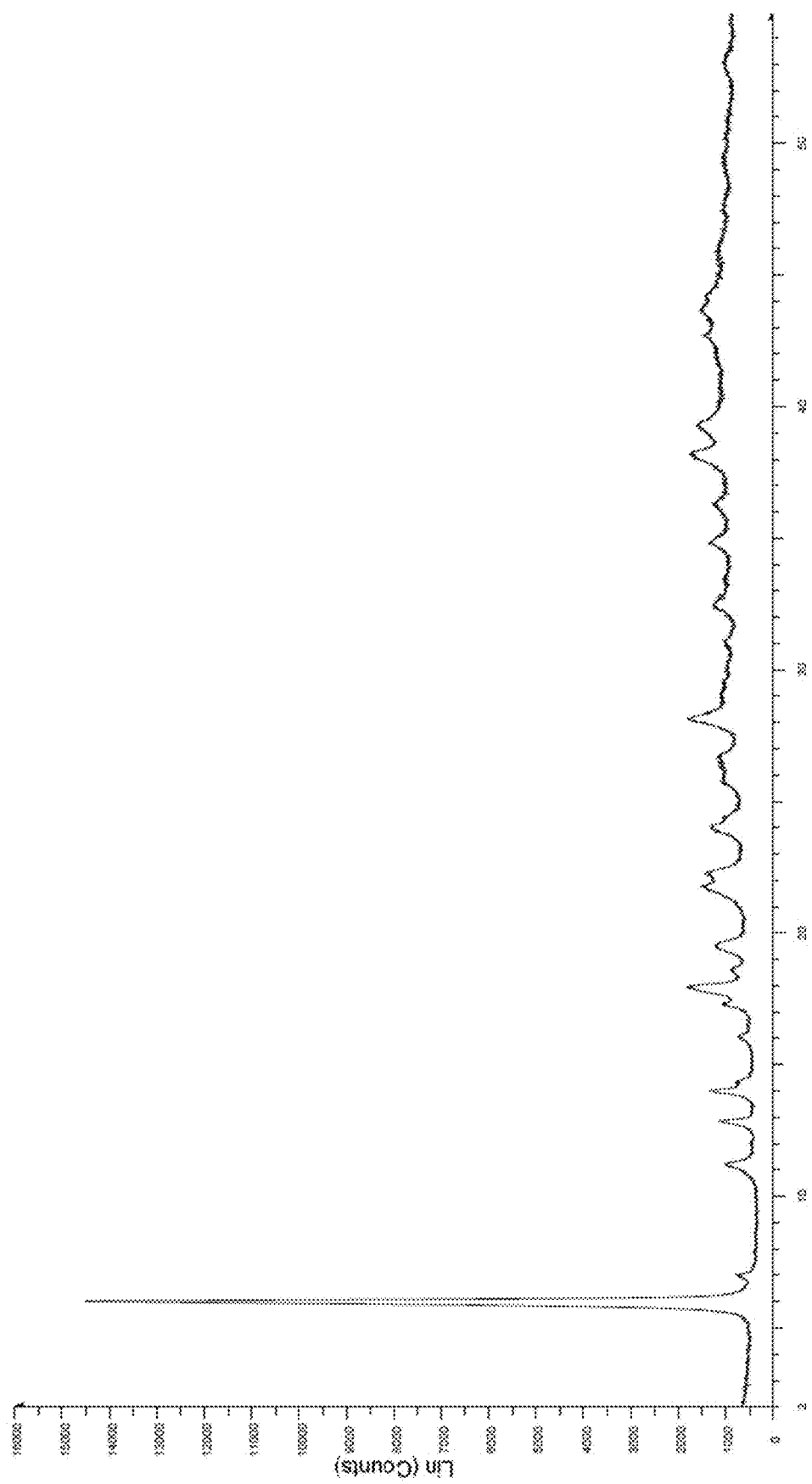
FIG. 6 shows a powder XRD for crystalline Dolutegravir potassium form III.
Figure 6A:
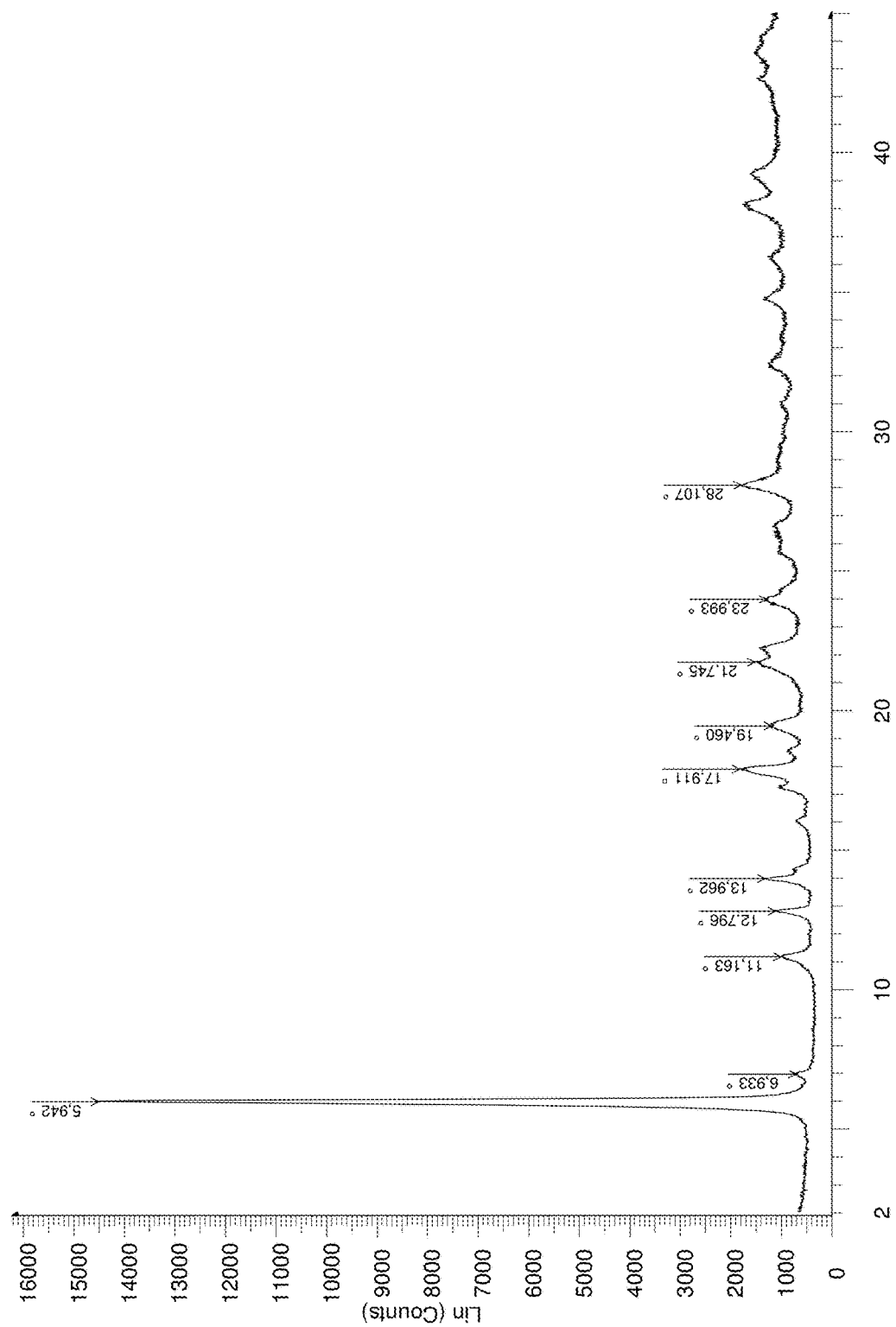
FIG. 6A shows a powder XRD for crystalline Dolutegravir potassium form III.

The present invention further encompasses a crystalline form of Dolutegravir potassium salt, designated as Form III, characterized by data selected from one or more of the following: a PXRD pattern having peaks at 5.94, 11.2, 14.0, 17.9 and 28.1 degrees 2-theta±0.2 degrees 2-theta; a PXRD pattern as depicted in FIG. 6; and combinations of these data.

Alternatively, a crystalline form of Dolutegravir potassium salt, designated as Form III, may be characterized by data selected from one or more of the following: a PXRD pattern having peaks at 5.9, 11.2, 14.0, 17.9 and 28.1 degrees 2-theta±0.2 degrees 2-theta; a PXRD pattern as depicted in FIG. 6; and combinations of these data.

Crystalline Form III of Dolutegravir potassium salt may be further characterized by a DSC thermogram showing a broad endotherm at about 40° C. to about 117° C., a broad exotherm at about 314 to about 325° C. and an endotherm with a peak temperature at about 332° C.

Figure 7:
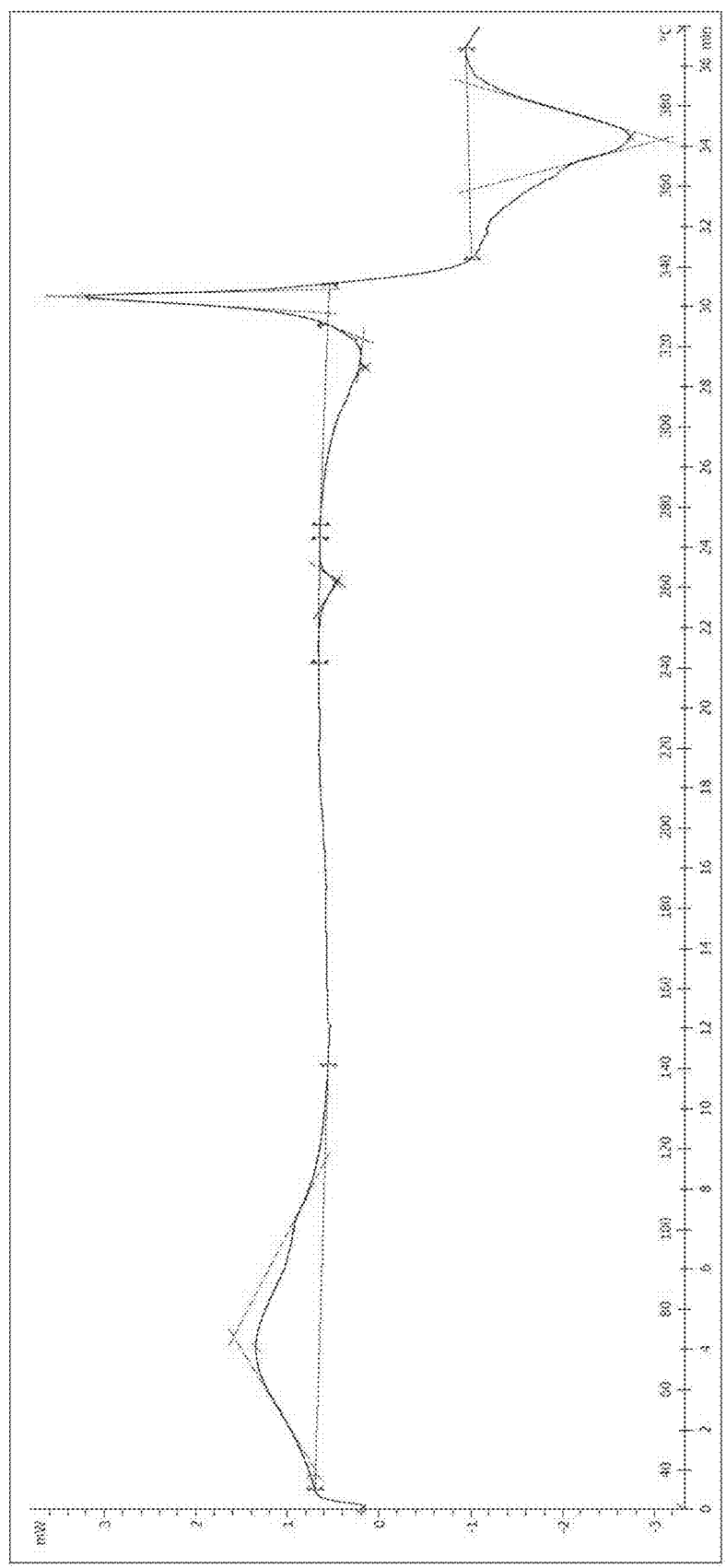
FIG. 7 shows a DSC thermogram for crystalline Dolutegravir potassium form III.
Figure 16:
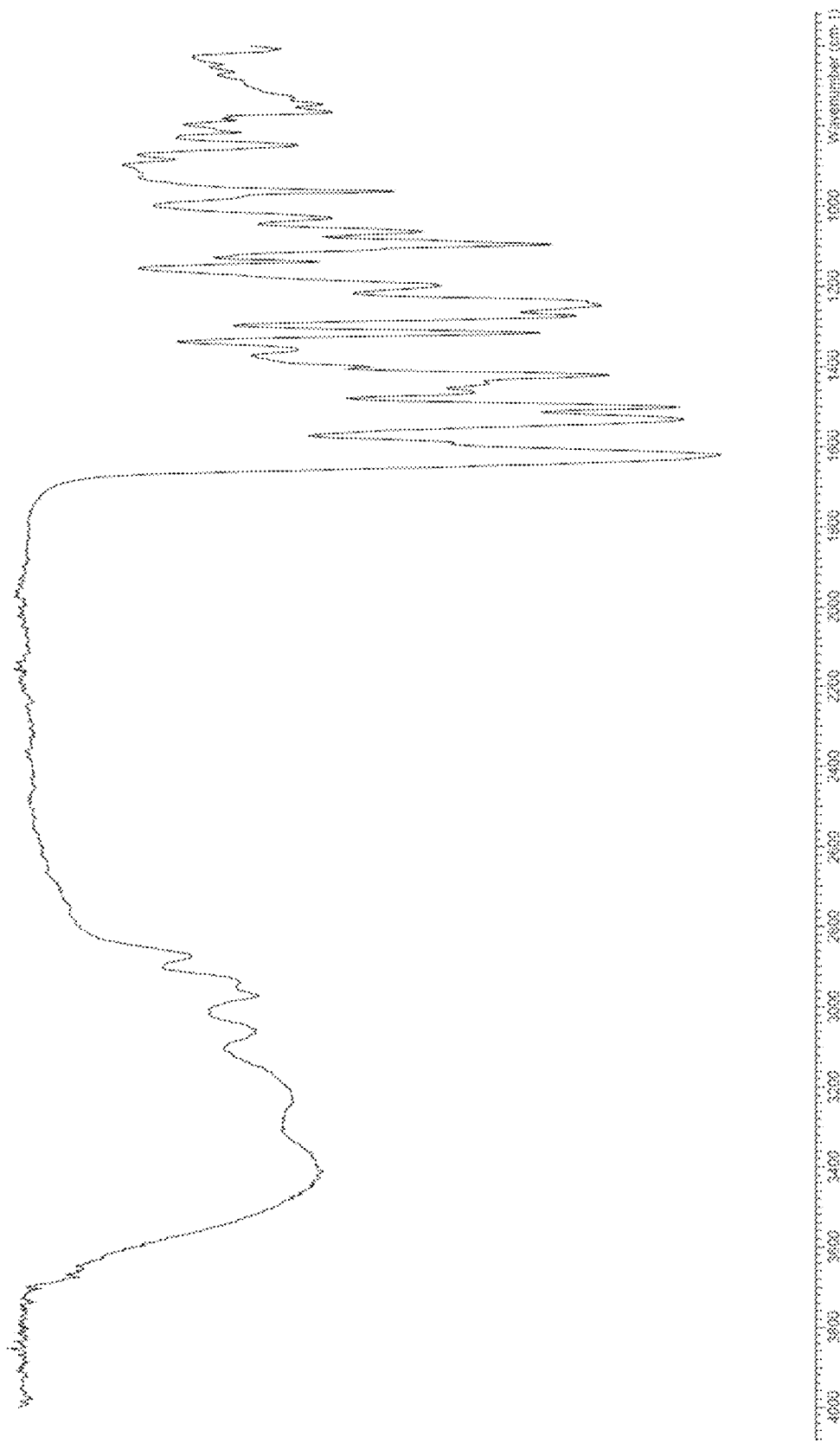
FIG. 16 shows an IR spectrum for Dolutegravir potassium Form III.

Crystalline Form III of Dolutegravir potassium salt may be further characterized by data selected from one or more of the following: a PXRD pattern having peaks at 5.94, 11.2, 14.0, 17.9 and 28.1 degrees 2-theta±0.2 degrees 2-theta, and also having one, two, three, four or five additional peaks selected from 6.93, 12.8, 19.5, 21.7 and 24.0 degrees two theta±0.2 degrees two theta; a DSC thermogram as depicted in FIG. 7; an FTIR spectrum as depicted in FIG. 16; and combinations of these data.

Alternatively, crystalline Form III of Dolutegravir potassium salt may be further characterized by data selected from one or more of the following: a PXRD pattern having peaks at 5.9, 11.2, 14.0, 17.9 and 28.1 degrees 2-theta±0.2 degrees 2-theta, and also having one, two, three, four or five additional peaks selected from 6.9, 12.8, 19.5, 21.7 and 24.0 degrees two theta±0.2 degrees two theta; a DSC thermogram as depicted in FIG. 7; an FTIR spectrum as depicted in FIG. 16; and combinations of these data.

Crystalline Form III of Dolutegravir potassium salt may be characterized by each of the above characteristics alone and/or by all possible combinations, e.g. by an X-ray powder diffraction pattern having peaks at 5.94, 11.2, 14.0, 17.9 and 28.1 degrees two theta±0.2 degrees two theta and an X-ray powder diffraction pattern as depicted in FIG. 6.

Figure 8:
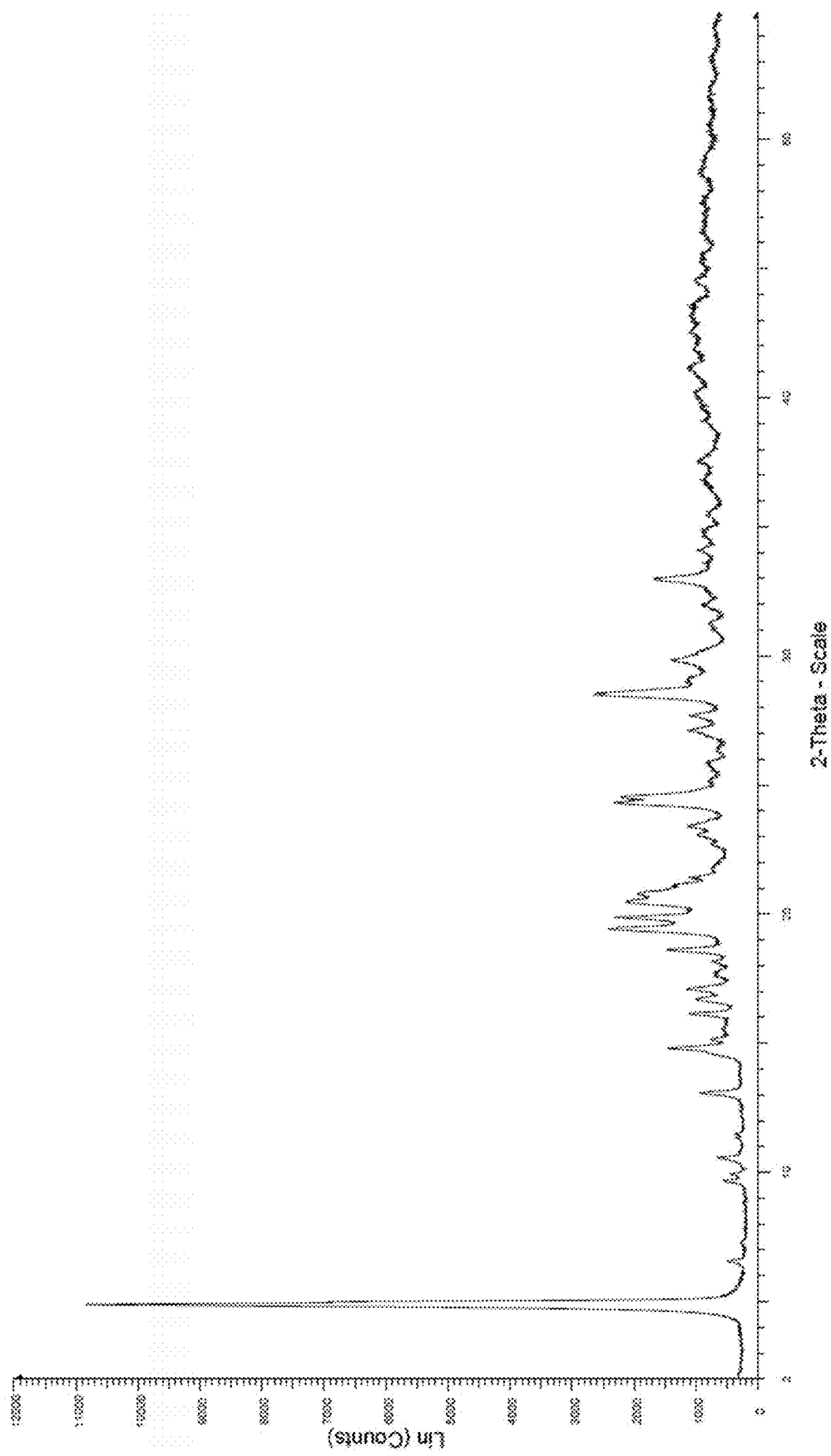
FIG. 8 shows a powder XRD for crystalline Dolutegravir potassium form IV.
Figure 8A:
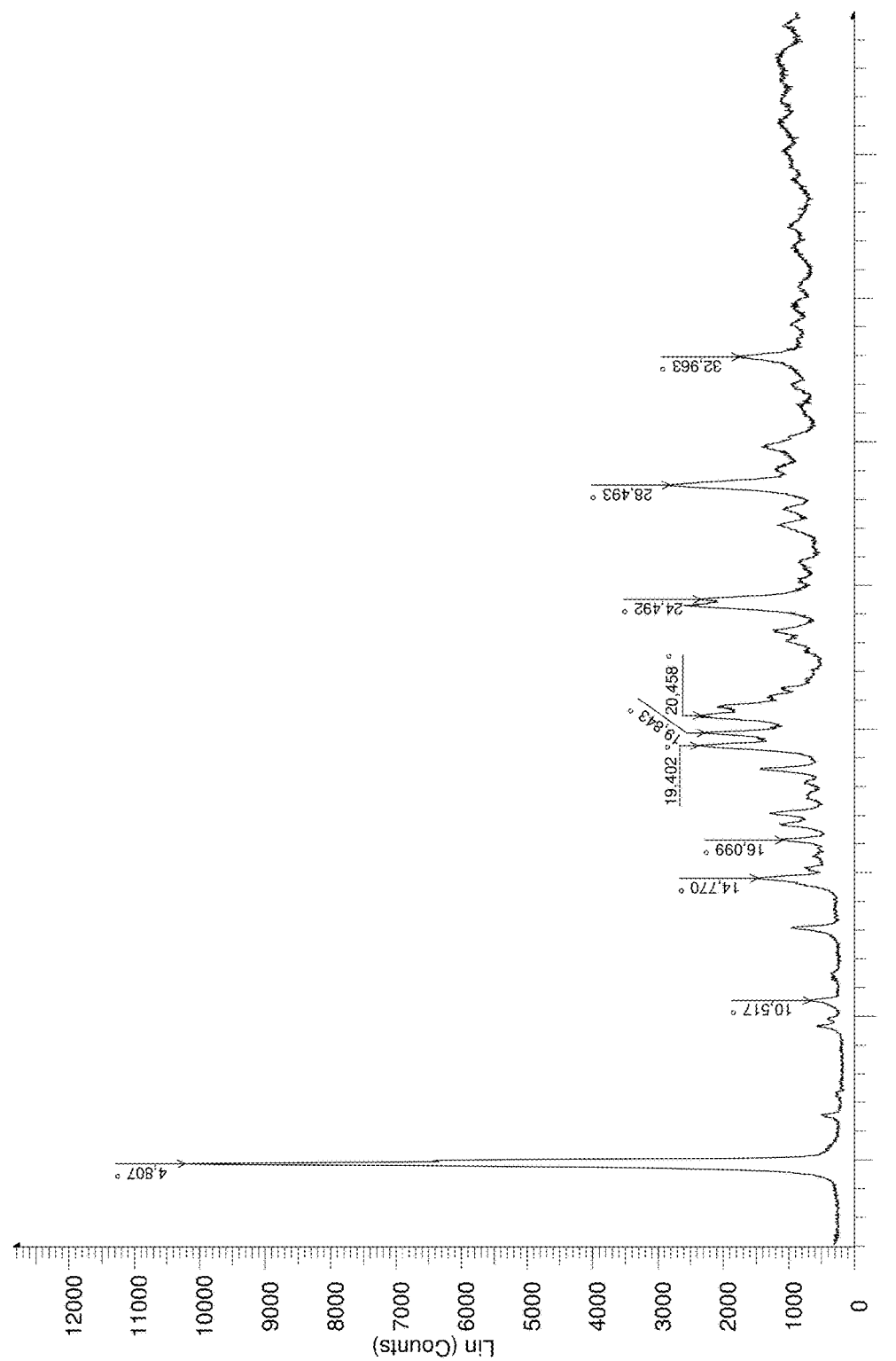
FIG. 8A shows a powder XRD for crystalline Dolutegravir potassium form IV.

The present invention further encompasses a crystalline form of Dolutegravir potassium salt, designated as Form IV, characterized by data selected from one or more of the following: a PXRD pattern having peaks at 4.83, 16.1, 19.4, 28.5 and 33.0 degrees 2-theta±0.2 degrees 2-theta; a PXRD pattern as depicted in FIG. 8; and combinations of these data.

Alternatively, a crystalline form of Dolutegravir potassium salt, designated as Form IV, may be characterized by data selected from one or more of the following: a PXRD pattern having peaks at 4.8, 16.1, 19.4, 28.5 and 33.0 degrees 2-theta±0.2 degrees 2-theta; a PXRD pattern as depicted in FIG. 8; and combinations of these data.

Crystalline Form IV of Dolutegravir potassium salt may be further characterized by a DSC thermogram showing a broad endotherm at about 180° C. to about 215° C., a broad exotherm at about 294 to about 324° C., and an endotherm with a peak temperature of about 328° C.

Figure 9:
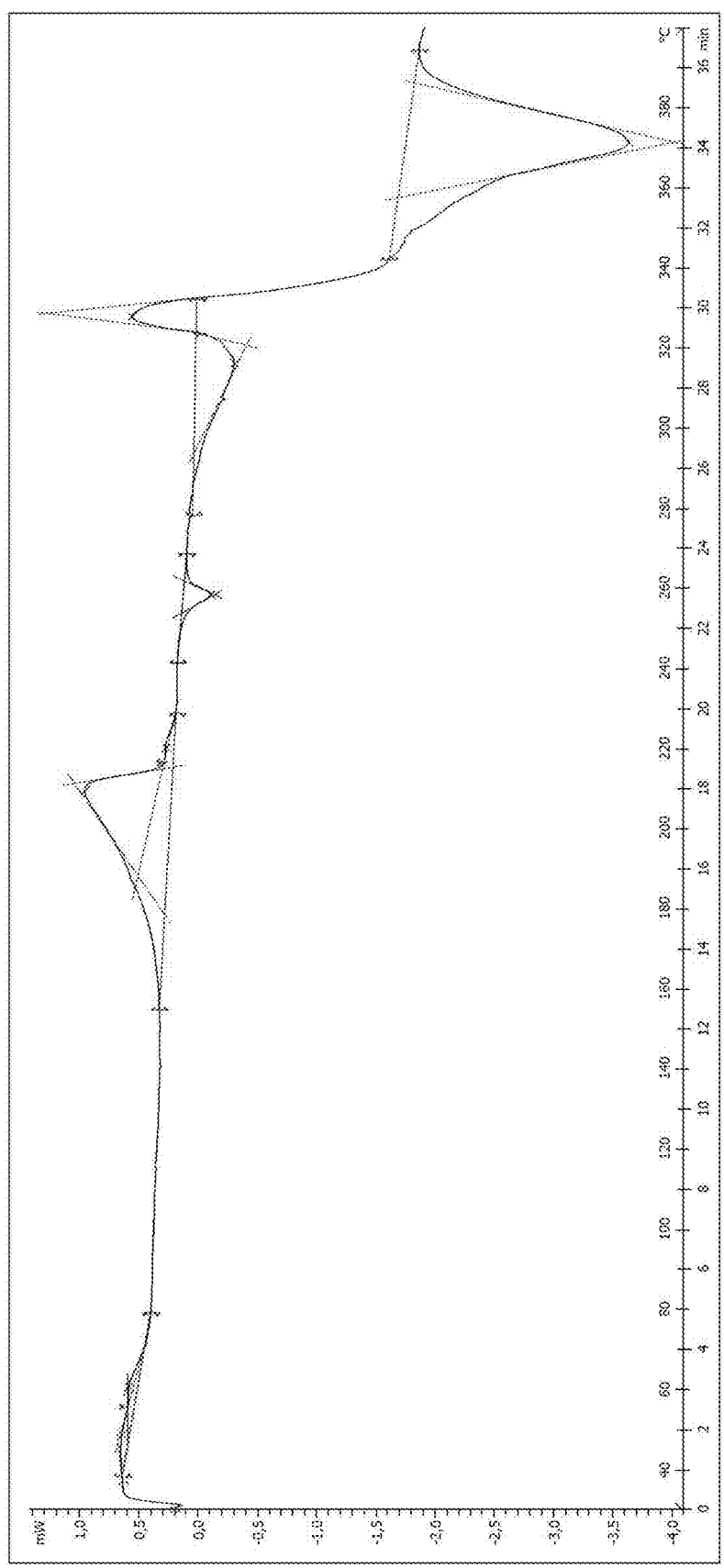
FIG. 9 shows a DSC thermogram for crystalline Dolutegravir potassium form IV.
Figure 10:
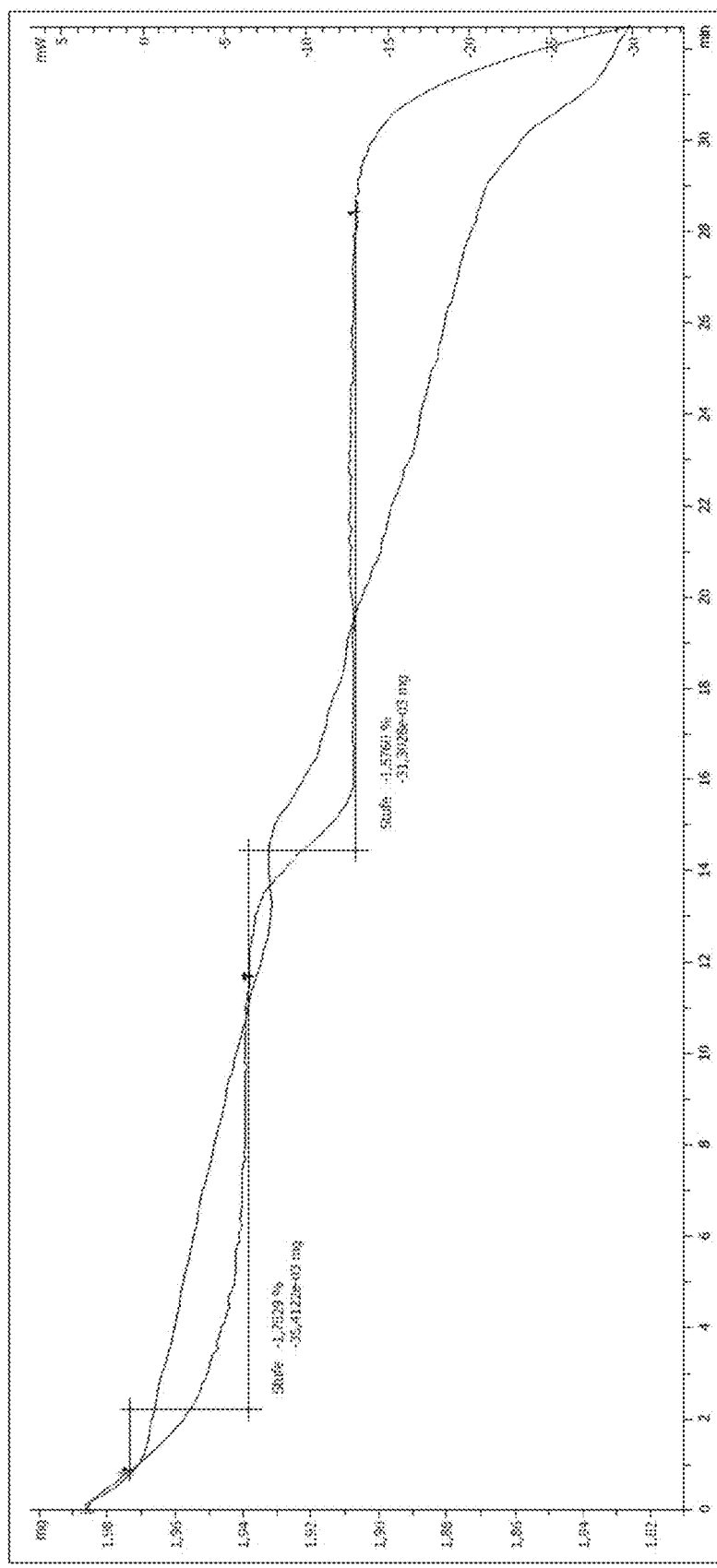
FIG. 10 shows a thermogravimetric analyses (TGA) for crystalline Dolutegravir potassium form IV.
Figure 17:
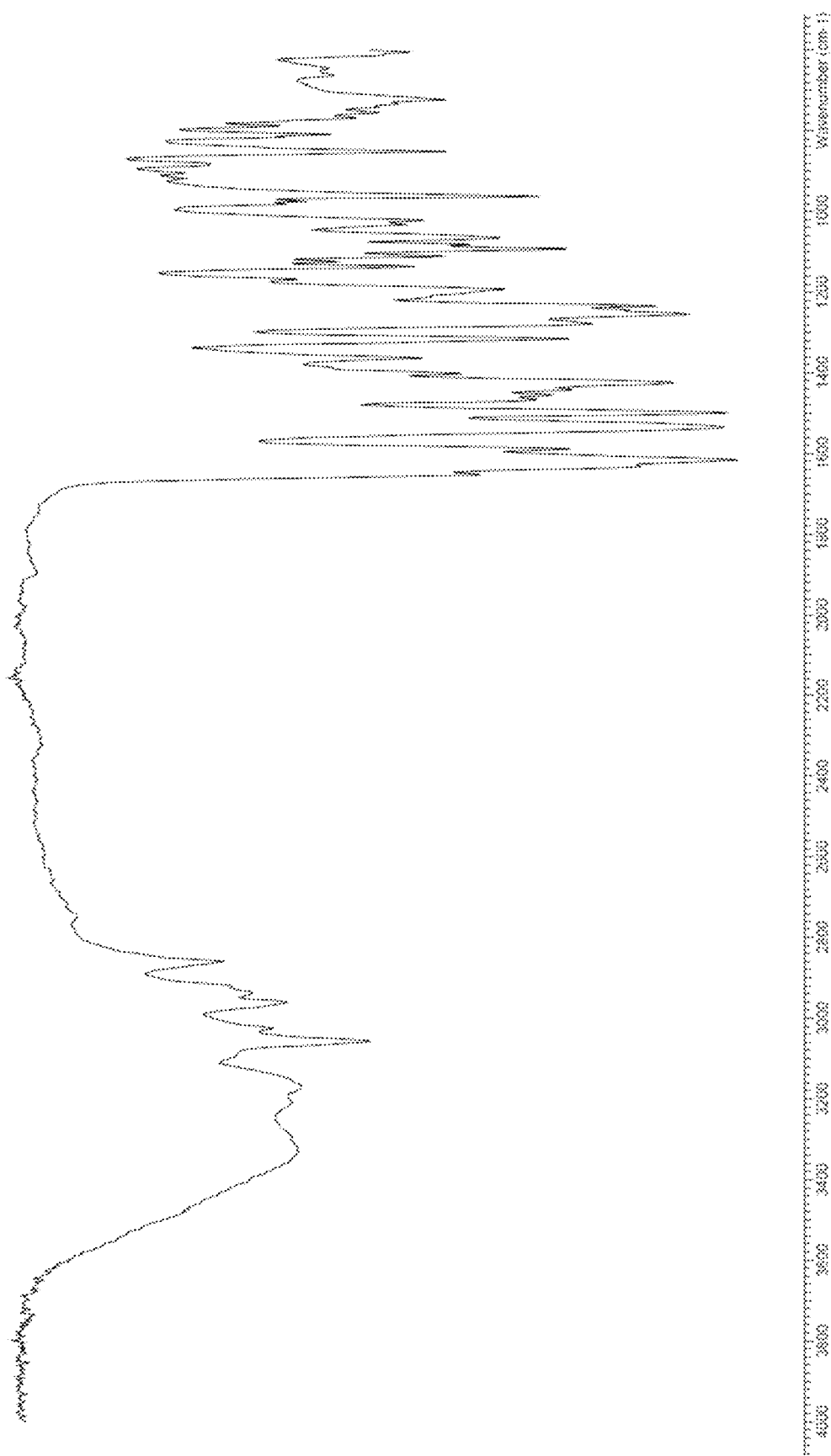
FIG. 17 shows an IR spectrum for Dolutegravir potassium Form IV.

Crystalline Form IV of Dolutegravir potassium salt may be further characterized by data selected from one or more of the following: a PXRD pattern having peaks at 4.83, 16.1, 19.4, 28.5 and 33.0 degrees 2-theta±0.2 degrees 2-theta, and also having one, two, three, four or five additional peaks selected from 10.5, 14.8, 19.8, 20.5 and 24.5 degrees two theta±0.2 degrees two theta; a DSC thermogram as depicted in FIG. 9; a TGA thermogram as depicted in FIG. 10; an FTIR spectrum as depicted in FIG. 17; and combinations of these data.

Alternatively, Crystalline Form IV of Dolutegravir potassium salt may be further characterized by data selected from one or more of the following: a PXRD pattern having peaks at 4.8, 16.1, 19.4, 28.5 and 33.0 degrees 2-theta±0.2 degrees 2-theta, and also having one, two, three, four or five additional peaks selected from 10.5, 14.8, 19.8, 20.5 and 24.5 degrees two theta±0.2 degrees two theta; a DSC thermogram as depicted in FIG. 9; a TGA thermogram as depicted in FIG. 10; an FTIR spectrum as depicted in FIG. 17; and combinations of these data.

Crystalline Form IV of Dolutegravir potassium salt may be characterized by each of the above characteristics alone and/or by all possible combinations, e.g. by an X-ray powder diffraction pattern having peaks at 4.83, 16.1, 19.4, 28.5 and 33.0 degrees two theta±0.2 degrees two theta and an X-ray powder diffraction pattern as depicted in FIG. 8.

As discussed above, Dolutegravir potassium form IV has some advantages. In particular, crystalline Form IV may be non-hygroscopic. Preferably, Dolutegravir potassium Form IV absorbs less than 3%, or less than 2%, or for example less than 1% (w/w) upon exposure to a temperature of 25° C. and 75% RH for about 24 hours and preferably 48 hours, as determined for example by TGA Additionally, crystalline Form IV can be stable upon storage at 45° C./75% relative humidity for a period of at least 8 weeks. Thus, preferably, following storage at 45° C./75% relative humidity for a period of at least 8 weeks Dolutegravir potassium Form IV contains less than 20%, less than 10%, less than 5%, less than 1%, or less than 0.5% by weight of any solid state form of Dolutegravir potassium as measured by XRPD.

Figure 11:
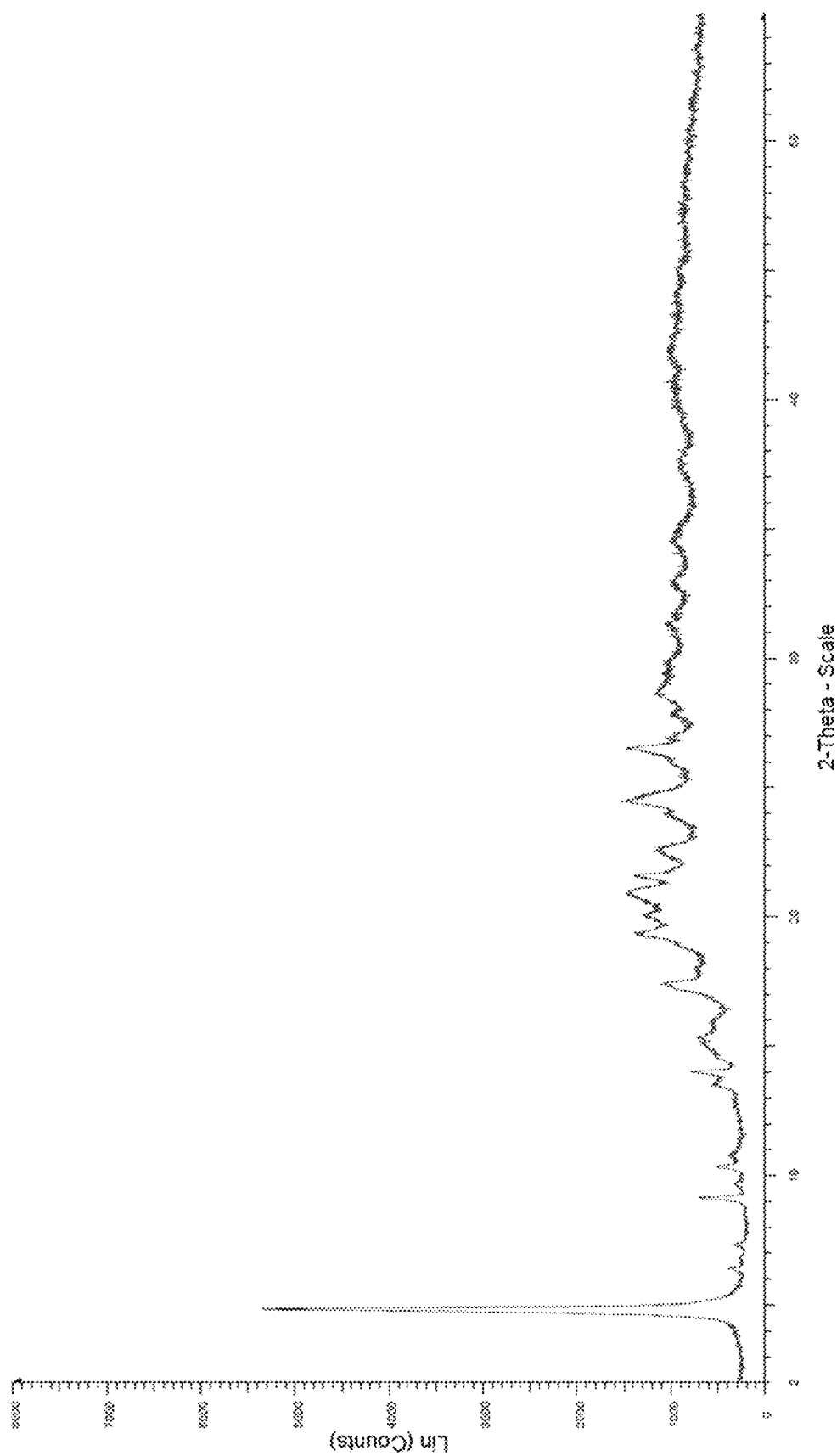
FIG. 11 shows a powder XRD for crystalline Dolutegravir potassium form V.

The present invention further encompasses a crystalline form of Dolutegravir potassium salt, designated as Form V, characterized by data selected from one or more of the following: a PXRD pattern having peaks at 4.76, 9.08, 14.0, 17.3 and 26.5 degrees 2-theta±0.2 degrees 2-theta; a PXRD pattern as depicted in FIG. 11; and combinations of these data.

Alternatively, a crystalline form of Dolutegravir potassium salt, designated as Form V, may be characterized by data selected from one or more of the following: a PXRD pattern having peaks at 4.8, 9.1, 14.0, 17.3 and 26.5 degrees 2-theta±0.2 degrees 2-theta; a PXRD pattern as depicted in FIG. 11; and combinations of these data.

Crystalline Form V of Dolutegravir potassium salt may be further characterized by data selected from one or more of the following: a PXRD pattern having peaks at 4.76, 9.08, 14.0, 17.3 and 26.5 degrees 2-theta±0.2 degrees 2-theta, and also having one, two, three, four or five additional peaks selected from 10.3, 19.3, 20.9, 21.5 and 24.5 degrees two theta±0.2 degrees two theta; and combinations of these data.

Alternatively, crystalline Form V of Dolutegravir potassium salt may be further characterized by data selected from one or more of the following: a PXRD pattern having peaks at 4.8, 9.1, 14.0, 17.3 and 26.5 degrees 2-theta±0.2 degrees 2-theta, and also having one, two, three, four or five additional peaks selected from 10.3, 19.3, 20.9, 21.5 and 24.5 degrees two theta±0.2 degrees two theta; and combinations of these data. Crystalline Form V of Dolutegravir potassium salt may be characterized by each of the above characteristics alone and/or by all possible combinations, e.g. by an X-ray powder diffraction pattern having peaks at 4.76, 9.08, 14.0, 17.3 and 26.5 degrees two theta±0.2 degrees two theta and an X-ray powder diffraction pattern as depicted in FIG. 11.

Figure 12:
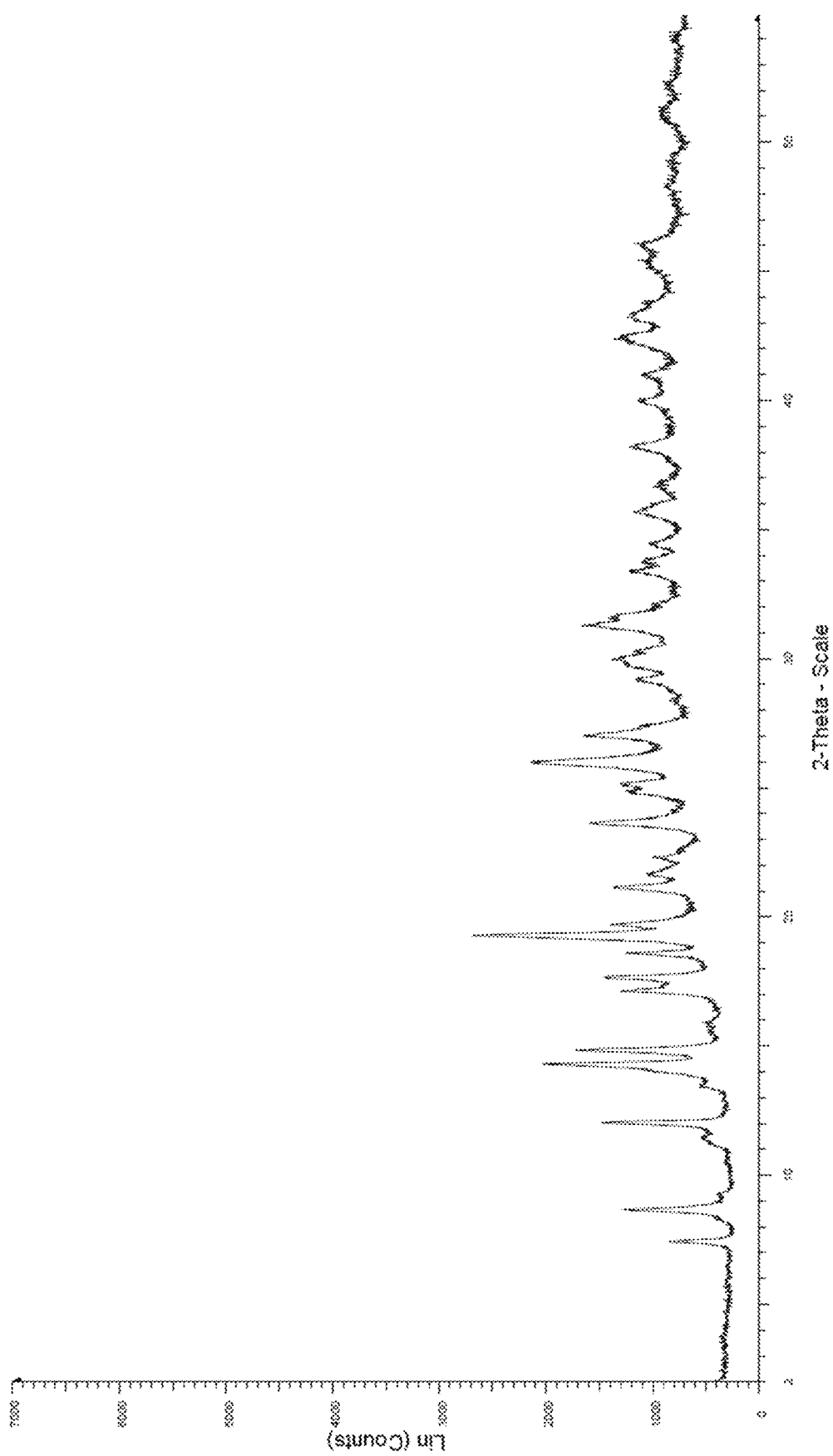
FIG. 12 shows a powder XRD for crystalline Dolutegravir potassium form VI.
Figure 12A:
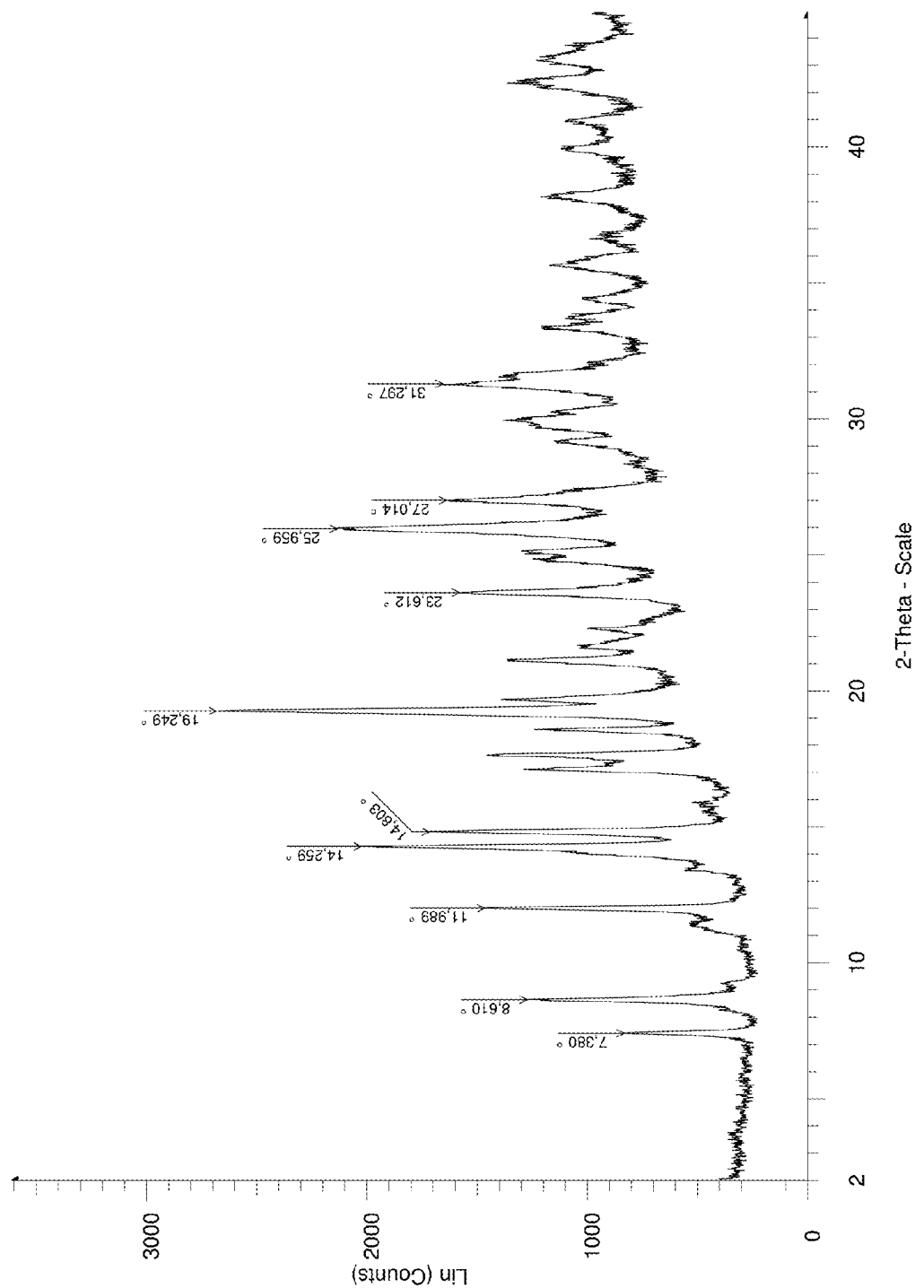
FIG. 12A shows a powder XRD for crystalline Dolutegravir potassium form VI.

The present invention further encompasses a crystalline form of Dolutegravir potassium salt, designated as Form VI, characterized by data selected from one or more of the following: a PXRD pattern having peaks at 8.61, 12.0, 14.3, 19.2 and 26.0 degrees 2-theta±0.2 degrees 2-theta; a PXRD pattern as depicted in FIG. 12; and combinations of these data.

Alternatively, a crystalline form of Dolutegravir potassium salt, designated as Form VI, may be characterized by data selected from one or more of the following: a PXRD pattern having peaks at 8.6, 12.0, 14.3, 19.2 and 26.0 degrees 2-theta±0.2 degrees 2-theta; a PXRD pattern as depicted in FIG. 12; and combinations of these data.

Crystalline Form VI of Dolutegravir potassium salt may be further characterized by a DSC thermogram showing a very broad endotherm between about 40° C. to about 145° C. (±2° C.), a very small exotherm between 259° C. and 266° C. (±2° C.), an endotherm with an onset temperature at about 326.5° (±0.5° C.) and a peak temperature of about 332.4° C. (±0.5° C.), followed by a broad exotherm, which corresponds to decomposition of the sample.

Figure 13:
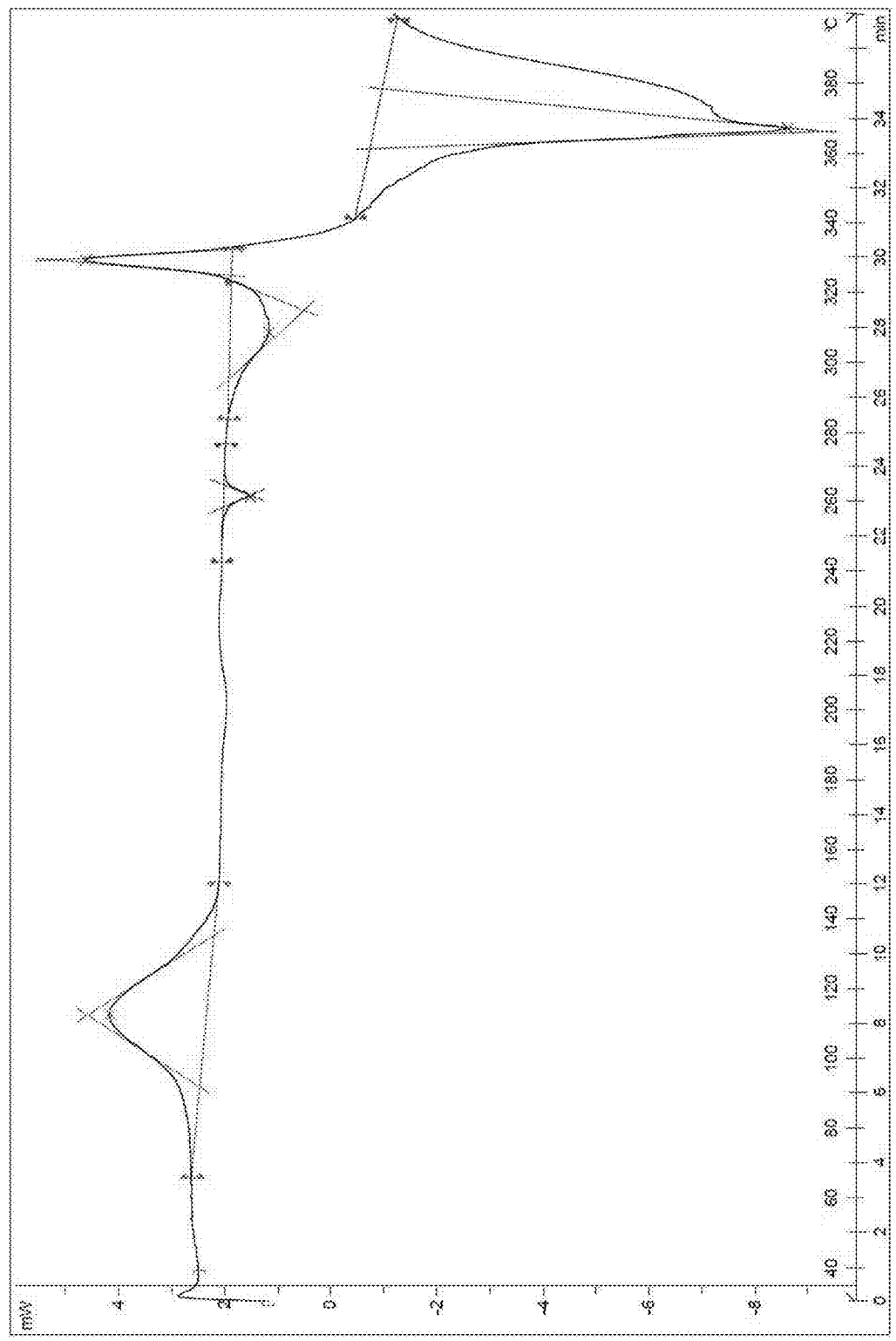
FIG. 13 shows a DSC thermogram for crystalline Dolutegravir potassium form VI.
Figure 14:
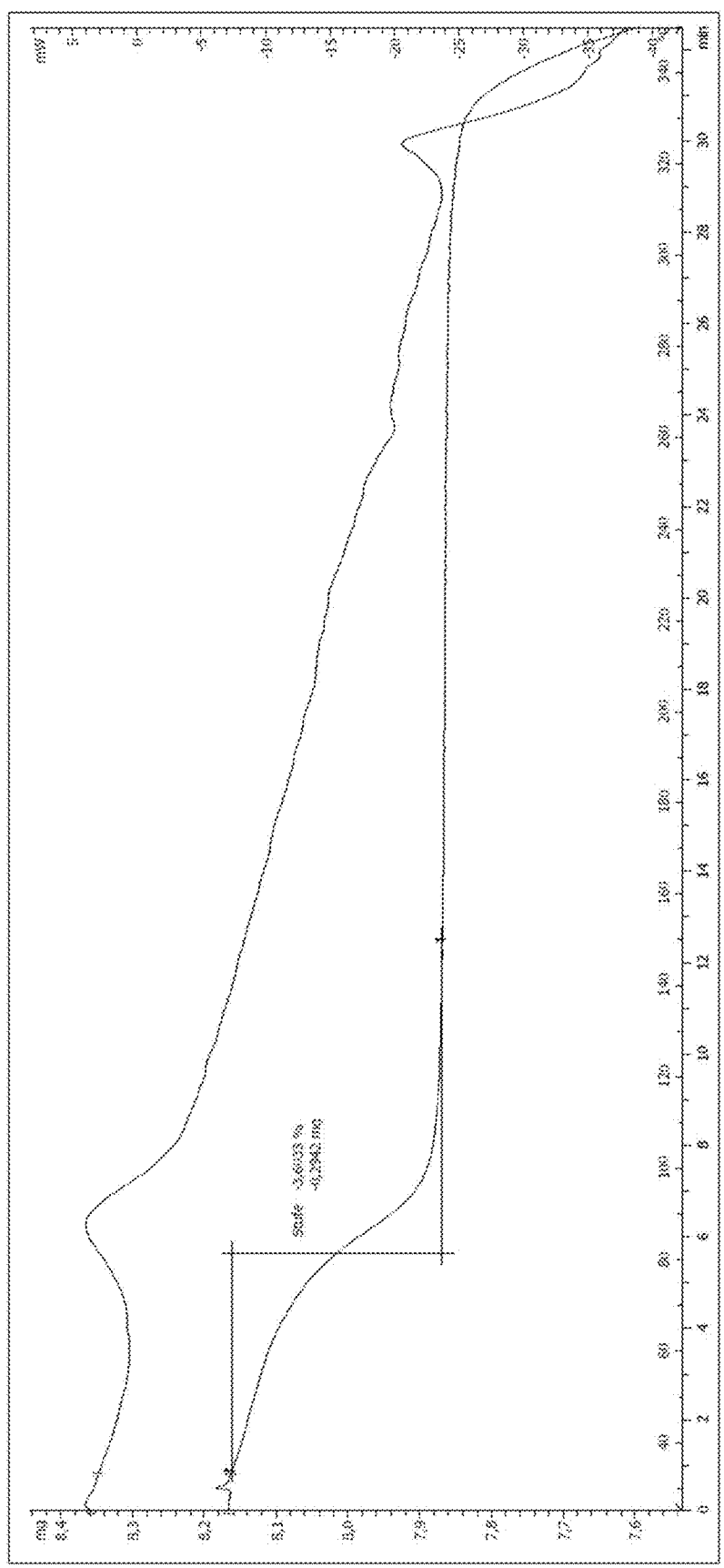
FIG. 14 shows a TGA for crystalline Dolutegravir potassium form VI.
Figure 18:
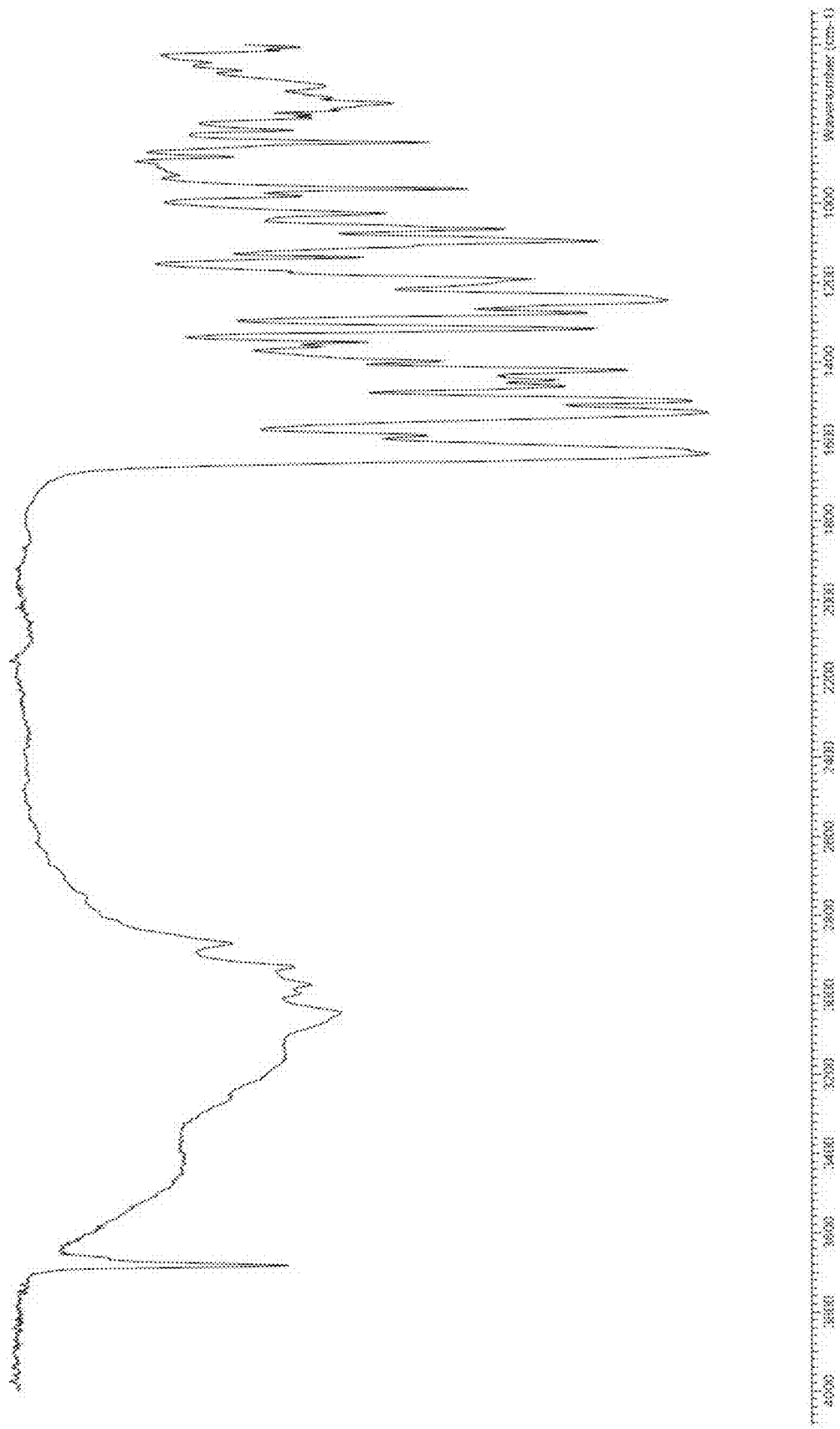
FIG. 18 shows an IR spectrum for Dolutegravir potassium Form VI.

Crystalline Form VI of Dolutegravir potassium salt may be further characterized by data selected from one or more of the following: a PXRD pattern having peaks at 8.61, 12.0, 14.3, 19.2 and 26.0 degrees 2-theta±0.2 degrees 2-theta, and also having one, two, three, four or five additional peaks selected from 7.38, 14.8, 23.6, 27.0 and 31.3 degrees two theta±0.2 degrees two theta; a DSC thermogram as depicted in FIG. 13; a TGA thermogram as depicted in FIG. 14; an FTIR spectrum as depicted in FIG. 18; and combinations of these data.

Alternatively, crystalline Form VI of Dolutegravir potassium salt may be further characterized by data selected from one or more of the following: a PXRD pattern having peaks at 8.6, 12.0, 14.3, 19.2 and 26.0 degrees 2-theta±0.2 degrees 2-theta, and also having one, two, three, four or five additional peaks selected from 7.4, 14.8, 23.6, 27.0 and 31.3 degrees two theta±0.2 degrees two theta; a DSC thermogram as depicted in FIG. 13; a TGA thermogram as depicted in FIG. 14; an FTIR spectrum as depicted in FIG. 18; and combinations of these data.

Crystalline Form VI of Dolutegravir potassium salt may be characterized by each of the above characteristics alone and/or by all possible combinations, e.g. by an X-ray powder diffraction pattern having peaks at 8.61, 12.0, 14.3, 19.2 and 26.0 degrees two theta±0.2 degrees two theta and an X-ray powder diffraction pattern as depicted in FIG. 12.

Crystalline Form VI of Dolutegravir potassium may be a monohydrate.

Figure 19:
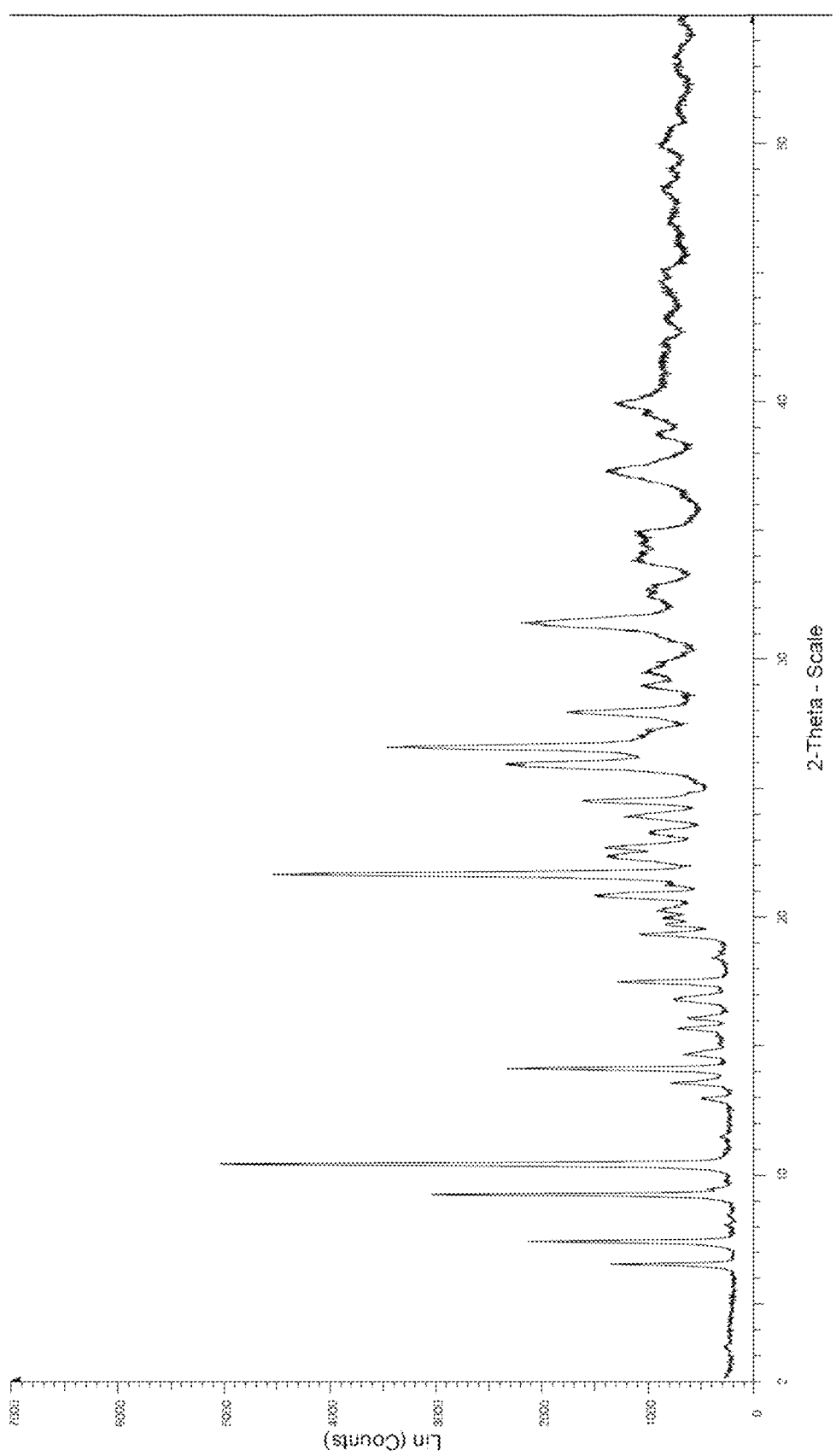
FIG. 19 shows a powder XRD for crystalline Dolutegravir potassium Form VII.
Figure 19A:
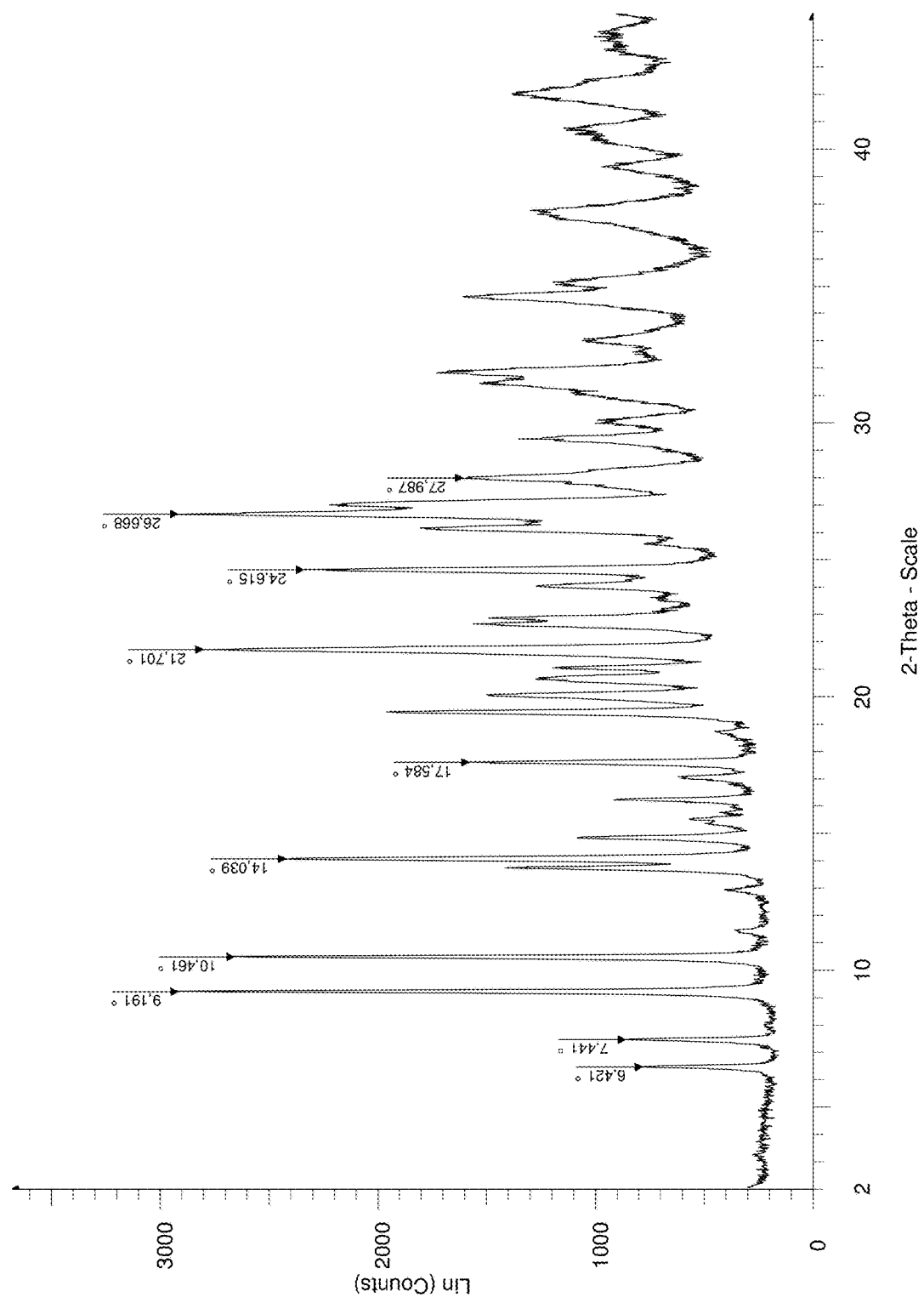
FIG. 19A shows a powder XRD for crystalline Dolutegravir potassium Form VII.

The present invention further encompasses a crystalline form of Dolutegravir potassium salt, designated as Form VII, characterized by data selected from one or more of the following: a PXRD pattern having peaks at 6.49, 9.19, 10.4, 21.6 and 26.6 degrees 2-theta±0.2 degrees 2-theta; a PXRD pattern as depicted in FIG. 19; and combinations of these data.

Alternatively, a crystalline form of Dolutegravir potassium salt, designated as Form VII, may be characterized by data selected from one or more of the following: a PXRD pattern having peaks at 6.5, 9.2, 10.4, 21.6 and 26.6 degrees 2-theta±0.2 degrees 2-theta; a PXRD pattern as depicted in FIG. 19; and combinations of these data.

Crystalline Form VII of Dolutegravir potassium salt may be further characterized by a DSC thermogram showing a very broad endotherm between about 40° C. to about 140° C. (±2° C.), a very small exotherm between 260° C. and 267° C. (±2° C.), an endotherm with an onset temperature at about 327.5° (±0.5° C.) and a peak temperature of about 331.9° C. (±0.5° C.), followed by a broad exotherm, which corresponds to decomposition of the sample.

Figure 20:
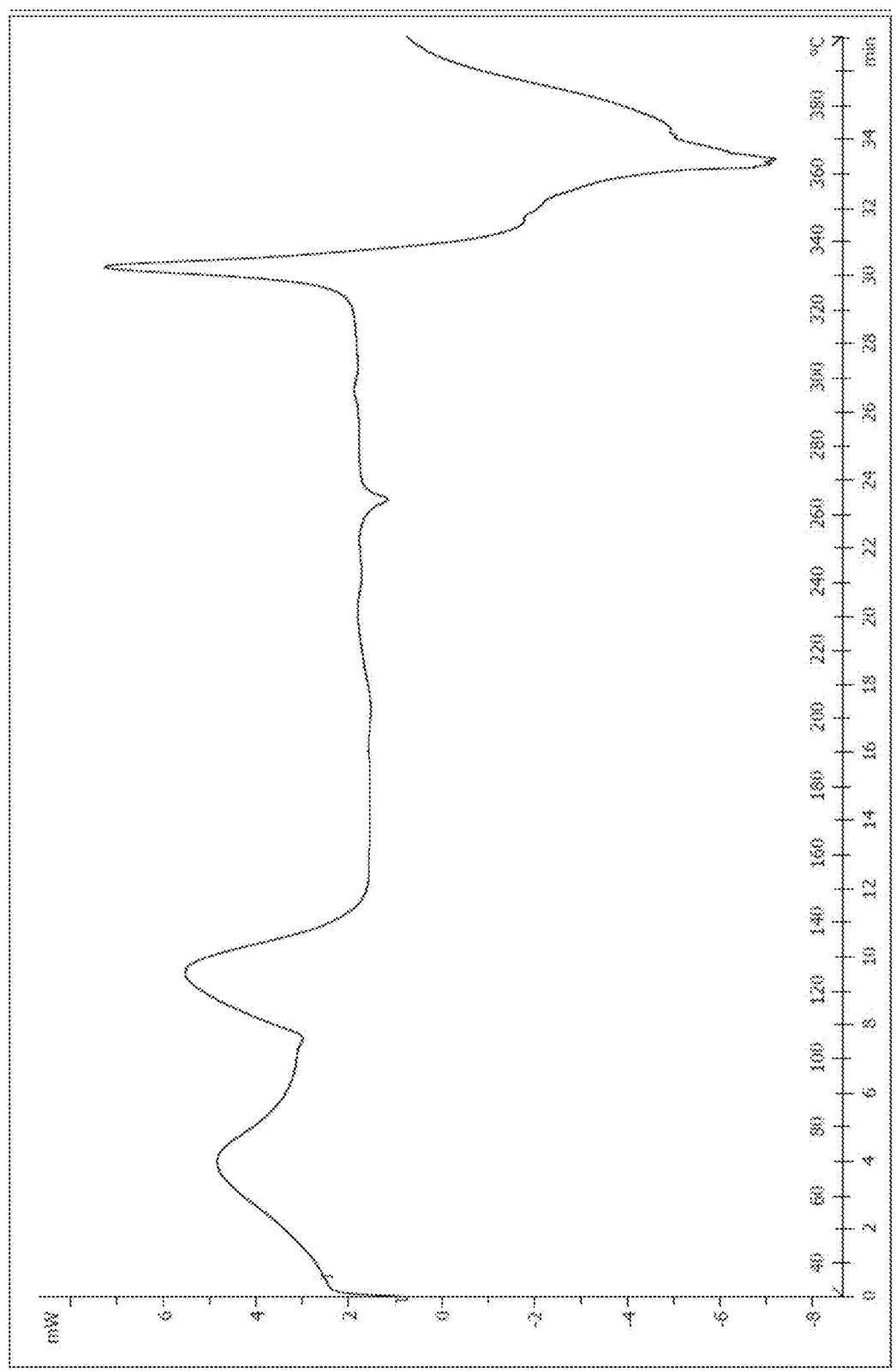
FIG. 20 shows a DSC thermogram for crystalline Dolutegravir potassium Form VII.
Figure 21:
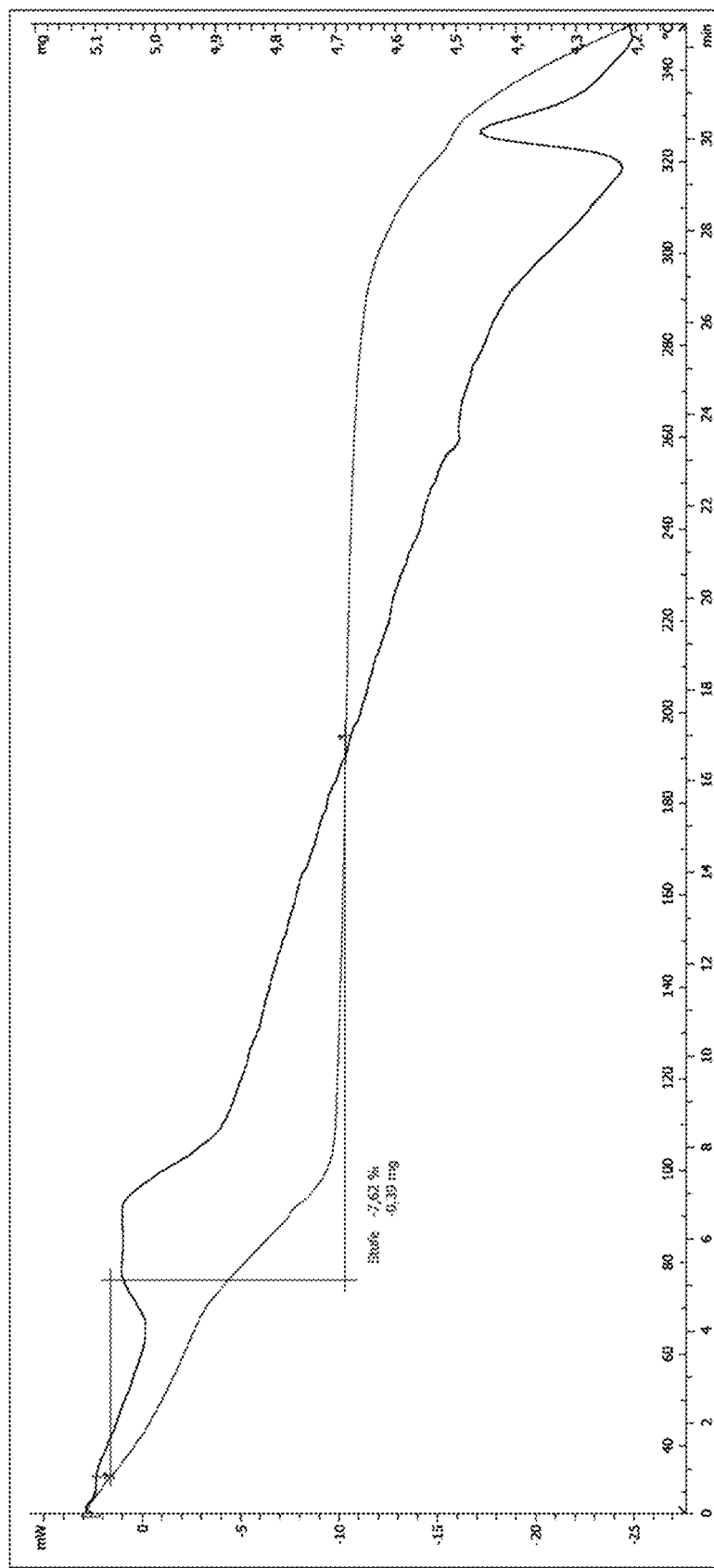
FIG. 21 shows a TGA for crystalline Dolutegravir potassium Form VII.
Figure 22:
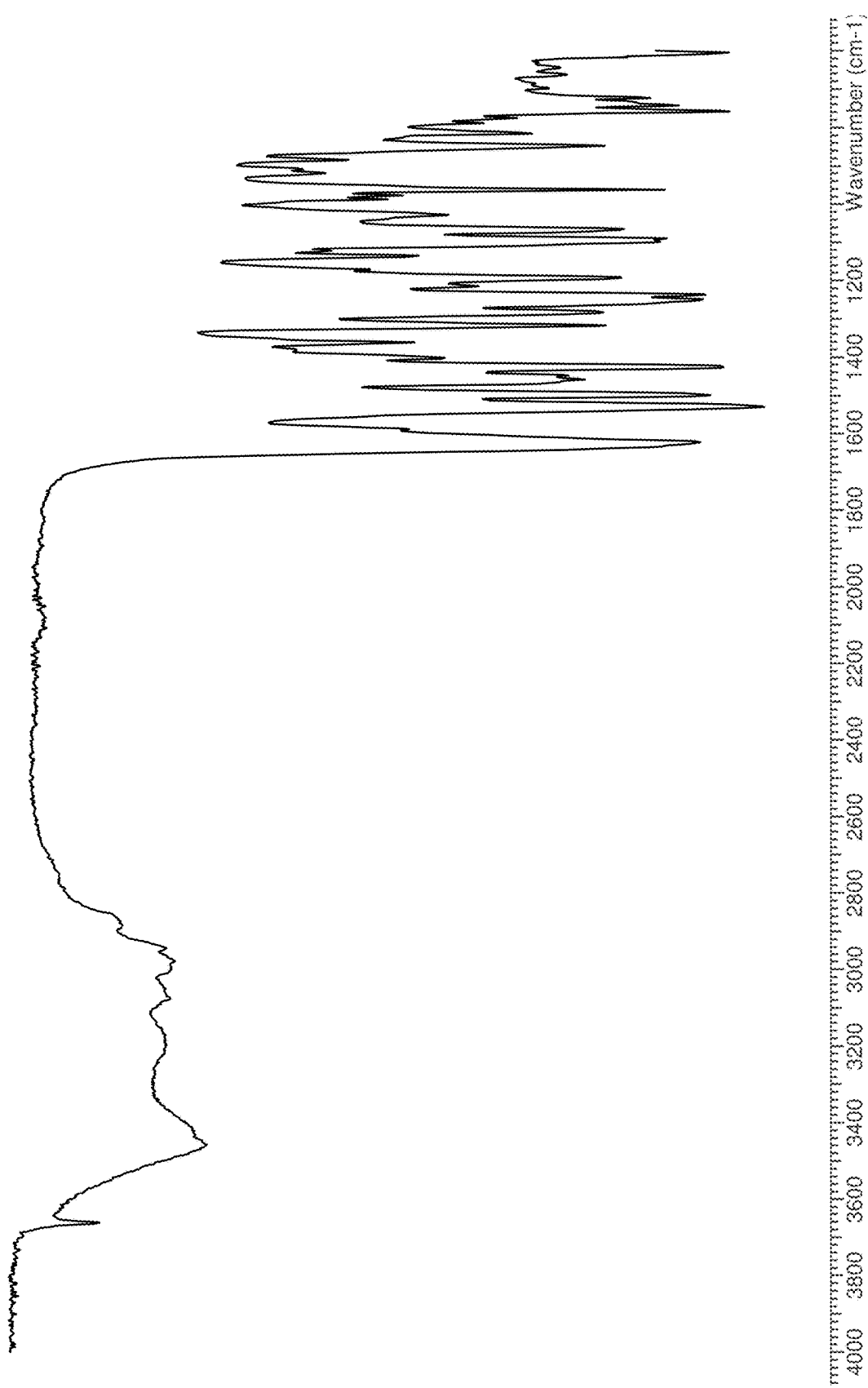
FIG. 22 shows an IR spectrum for Dolutegravir potassium Form VII.

Crystalline Form VII of Dolutegravir potassium salt may be further characterized by data selected from one or more of the following: a PXRD pattern having peaks at 6.49, 9.19, 10.4, 21.6 and 26.6 degrees 2-theta±0.2 degrees 2-theta, and also having one, two, three, four or five additional peaks selected from 7.36, 14.1, 17.5, 24.5 and 27.9 degrees two theta±0.2 degrees two theta; a DSC thermogram as depicted in FIG. 20; a TGA thermogram as depicted in FIG. 21; an FTIR spectrum as depicted in FIG. 22; and combinations of these data.

Alternatively, crystalline Form VII of Dolutegravir potassium salt may be further characterized by data selected from one or more of the following: a PXRD pattern having peaks at 6.5, 9.2, 10.4, 21.6 and 26.6 degrees 2-theta±0.2 degrees 2-theta, and also having one, two, three, four or five additional peaks selected from 7.4, 14.1, 17.5, 24.5 and 27.9 degrees two theta±0.2 degrees two theta; a DSC thermogram as depicted in FIG. 20; a TGA thermogram as depicted in FIG. 21; an FTIR spectrum as depicted in FIG. 22; and combinations of these data.

Additionally, Crystalline Form VII of Dolutegravir potassium salt may further be characterized by the absence of one, two, three, four or five XPRD peaks selected from 4.8, 6.0, 6.9, 8.6 and 12.0 degrees two theta±0.2 degrees two theta.

Crystalline Form VII of Dolutegravir potassium salt may be characterized by each of the above characteristics alone and/or by all possible combinations, e.g. by an X-ray powder diffraction pattern having peaks at 6.49, 9.19, 10.4, 21.6 and 26.6 degrees two theta±0.2 degrees two theta and an X-ray powder diffraction pattern as depicted in FIG. 19.

Crystalline Form VII of Dolutegravir potassium may be a dihydrate.

Preferably, the crystalline Form VII of Dolutegravir potassium as defined in any of the embodiments is polymorphically pure. In particular, Form VII is preferably substantially free of any other solid state (or polymorphic) forms of Dolutegravir potassium. Preferably, Form VII contains 20% or less, 10% or less, 5% or less, 2% or less, or 1% or less of any other forms of the subject compound as determined, for example, by XRPD. Especially, the Form VII is preferably substantially free (and therefore preferably contains 20% or less, 10% or less, 5% or less, 2% or less, or 1% or less) of Form IV of Dolutegravir potassium as defined herein. Thus, Form VII Dolutegravir potassium preferably contains greater than 80% (w/w), greater than 90% (w/w), greater than 95% (w/w), greater than 98% (w/w), or greater than 99% (w/w) of the subject solid state form of Dolutegravir. Accordingly, in some embodiments of the invention, the described solid state forms of Dolutegravir may contain from 1% to 20% (w/w), from 5% to 20% (w/w), or from 5% to 10% (w/w) of one or more other solid state forms of Dolutegravir (such as Form IV). Thus, in a particularly preferred embodiment, the Form VII Dolutegravir potassium of the present invention contains 20% or less, 10% or less, 5% or less, 2% or less, or 1% or less of any other forms of Dolutegravir potassium (particularly Form IV Dolutegravir potassium) as determined for example, by XRPD.

The polymorphic purity of crystalline Dolutegravir potassium Form VII can be determined by measuring the content of other forms of Dolutegravir potassium, particularly Form IV by PXRD. For example, a skilled person would measure the content of Dolutegravir potassium Form IV in crystalline Dolutegravir potassium Form VII by detecting and quantifying the characteristic peaks of Form IV.

The characteristic peaks of crystalline Dolutegravir potassium Form IV used for the above described measurement can be selected from the following list of peaks at about: 4.8, 9.6, 16.6, 18.1 and 28.5 degrees two theta±0.2 degrees two theta.

As discussed above, Dolutegravir potassium Form VII has some advantages. In particular the crystalline Form VII of Dolutegravir potassium may be stable upon storage. Preferably the crystalline Form VII is stable to conversion to other solid state/crystalline forms of Dolutegravir potassium. In particular, the crystalline Form VII is stable for at least 8 weeks under storage conditions of 25° C. and 60% relative humidity (RH), 30° C. and 65% RH and 40° C. and 75% RH. More preferably, following storage for least 8 weeks under storage conditions of 25° C. and 60% relative humidity (RH), 30° C. and 65% RH and 40° C. and 75% RH, the Dolutegravir potassium Form VII contains less than 20%, less than 10%, less than 5%, 1%, or less 0.5% by weight of any other solid state form of Dolutegravir potassium, as measured by XRPD.

The present invention encompasses a process for preparing Dolutegravir or other Dolutegravir salts or solid state forms. The process comprises preparing Dolutegravir potassium salt and any of the solid state forms of Dolutegravir potassium by the processes of the present invention, and converting it to said other Dolutegravir salt. The conversion can be done, for example, by a process comprising acidifying the above described Dolutegravir potassium salt and/or any one or a combination of the solid state forms thereof, and reacting the obtained Dolutegravir free acid with an appropriate base, to obtain the corresponding salt. Alternatively, the conversion can be done by salt switching, i.e., reacting the Dolutegravir potassium salt, with a base having a $pK_a$ which is higher than the $pK_a$ of the base of the Dolutegravir potassium salt.

The present invention also provides the use of the above described Dolutegravir potassium salt and any of the solid state forms of Dolutegravir potassium salt for preparing Dolutegravir or other Dolutegravir salts, and solid state forms thereof.

In another embodiment the present invention encompasses the above described Dolutegravir potassium salt or solid state forms of thereof for use in the preparation of pharmaceutical compositions, preferably for the treatment of HIV infection.

The present invention further provides pharmaceutical compositions comprising Dolutegravir potassium salt or one or more of the solid state forms thereof according to the present invention. Typically, the pharmaceutical composition is a solid composition and the Dolutegravir potassium salt retains its solid state forms.

The present invention encompasses a process to prepare a pharmaceutical composition of Dolutegravir potassium salt comprising combining Dolutegravir potassium salt or any one or a mixture of the above solid state forms.

In yet another embodiment, the present invention encompasses a pharmaceutical formulation comprising the above described Dolutegravir potassium salt or solid state forms of Dolutegravir potassium salt and at least one pharmaceutically acceptable excipient.

In another embodiment the present invention encompasses the use of the above described Dolutegravir potassium salt and solid state forms of Dolutegravir potassium salt for the preparation of pharmaceutical formulations.

The present invention comprises a process for preparing the above mentioned pharmaceutical formulations. The process comprises combining Dolutegravir potassium salt and solid state forms thereof, with at least one pharmaceutically acceptable excipient.

The Dolutegravir potassium salt and solid state forms as defined herein as well as the pharmaceutical compositions or formulations of Dolutegravir potassium salt can be used as medicaments, particularly for the treatment of HIV infection.

The present invention also provides a method of treating HIV infection, comprising administering a therapeutically effective amount of the Dolutegravir potassium salt and solid state forms thereof of the present invention, or at least one of the above pharmaceutical compositions or formulations, to a subject suffering from HIV infection, or otherwise in need of the treatment.

The present invention also provides the use of Dolutegravir potassium salt and solid state forms thereof of the present invention, or at least one of the above pharmaceutical compositions or formulations for the manufacture of a medicament for treating HIV infection.

Having described the invention with reference to certain preferred embodiments, other embodiments will become apparent to one skilled in the art from consideration of the specification. The invention is further illustrated by reference to the following examples describing in detail the preparation of the composition and methods of use of the invention. It will be apparent to those skilled in the art that many modifications, both to materials and methods, may be practiced without departing from the scope of the invention.

Nuclear Magnetic Resonance (NMR) Spectroscopy Method:
Instrument: Varian Mercury 400 Plus NMR Spectrometer, Oxford AS, 400 MHz.

Infrared Spectroscopy Method:
Instrument: Thermo Nicolet, Avatar 330 FT-IR, Smart Endurance Diamond-ATR
Scans number: 16
Scan begin: 400 cm-1
Scan end: 4000 cm-1
Software: Omnic Vers. 6.1a Differential Scanning Calorimetry (DSC) Method:
Instrument: Mettler Toledo DSC 822E coupled with a Mettler Toledo Gas-Flow-Controller TS0800GC1 (Mettler-Toledo GmbH, GieBen, Germany)
Aluminium crucible: 40 µL
Lid: perforated
Temperature range: 30° C. to 400° C.
Heating rate: 10° C./min
Nitrogen flush: 50 mL/min
Software: STARe Version. 8.10
Interpretation: Endothermic modus Powder X-Ray Diffraction Pattern ("PXRD") Method:
The sample was analyzed on a D8 Advance X-ray powder diffractometer (Bruker-AXS, Karlsruhe, Germany). The sample holder was rotated in a plane parallel to its surface at 20 rpm during the measurement. Further conditions for the measurements are summarized below. The raw data were analyzed with the program EVA (Bruker-AXS, Germany),

|  | Standard measurement |
| --- | --- |
| radiation | Cu K$_\alpha$ ($\lambda$ = 1.5418 Å) |
| source | 38 kV/40 mA |
| detector | Vantec |
| detector slit | Variable |
| divergence slit | v6 |
| antiscattering slit | v6 |
| 2θ range/° | 2 ≤ 2θ ≤ 55 |
| step size/° | 0.017 |

Thermogravimetric Analysis (TGA) Method:
Instrument: Mettler Toledo TGA/DSC1 (Mettler-Toledo GmbH, GieBen, Germany)
Aluminium crucible: 40 µL (open)
Temperature range: 25° C. to 350° C.
Heating rate: 10° C./min
Nitrogen flush: 50 mL/min
Software: STARe Version. 11.00

HPLC Method (for Determination of the Chemical Purity):
Instrument: Agilent 1200 (G3325)
Method: DOLUTEGRAVIR-7.M
Column: Waters Symmetry C18 3.5u 150*4.6 mm
Flow: 0.7 ml/min.
Temperature: 40.0° C.
Eluent
A: acetonitrile
B: 0.2% formic acid+0.1% HFBA

|  | Time [min] | eluent A [%] | eluent B [%] |
| --- | --- | --- | --- |
| Gradient: | 0.0 | 35 | 65 |
|  | 10.0 | 70 | 30 |
|  | 15.0 | 85 | 15 |
|  | 17.0 | 85 | 15 |
|  | 17.5 | 35 | 65 |
| Stop time | 23.0 |  |  |

Injection volume: 5
Detection: DAD ($\lambda$=258 nm)

In the following examples, unless otherwise indicated, the purity relates to chemical purity as determined by the above HPLC method.

Preferably, in the following examples, the term overnight refers to a period of about 12 to about 18 hours, typically about 16 hours.

EXAMPLES

Reference Examples

The starting material Dolutegravir (also referred to as Dolutegravir free acid) can for example be prepared by processes disclosed in WO 2010/068253 and US2012/0022251 or by the following process.

Preparation of 1-(2,2-dimethoxyethyl)-1,4-dihydro-4-oxo-3-(phenylmethoxy)-2,5-Pyridinedicarboxylic acid 5-ethyl ester 2-methyl ester A 10 L reactor was charged with 610.5 g of 4-benzyloxy-2-(1-dimethylamino-methylidene)-3-oxo-butyric acid ethyl ester (2.09 mol, 1.00 eq.), 494.0 g dimethyl oxalate (4.19 mol, 2.00 eq.) and 2.21 L DMSO. After dissolution of solids, the mixture was cooled to 15° C. and 453.0 g of sodium methoxide solution (30 wt % in methanol, 2.51 mol, 1.20 eq.) was added dropwise within 50 min. The mixture was warmed to 20° C. and stirred until complete consumption of starting material (approx. 1.5 h). In parallel, 628.4 g acetic acid (10.5 mol, 5.00 eq.) was added dropwise to a solution of 330.6 g 2,2-dimethoxyethylamine (3.14 mol, 1.50 eq.) in 860 ml THF, at room temperature. This solution was then added dropwise to the reactor within 45 min, at room temperature: The resulting mixture was then heated to 40° C. and further stirred until complete consumption of starting material (30 h). After cooling to room temperature, the reaction mixture was diluted with 3.6 L water and 4.5 L ethyl acetate. After decantation, the aqueous layer was extracted with ethyl acetate (1×1.3 L). The combined organic extracts were washed with 1 N NCl (2×0.8 L), water/brine (80/20 (v/v), 4×1.5 L), dried and concentrated to afford 891.0 g of crude 1-(2,2-dimethoxyethyl)-1,4-dihydro-4-oxo-3-(phenylmethoxy)-2,5-Pyridinedicarboxylic acid 5-ethyl ester 2-methyl ester (101.5% yield, chemical purity (HPLC/UV, λ=254 nm): 91.8%) as orange oil which was used in the next step without further purification.

Preparation of 1,4-dihydro-4-oxo-1-(2-oxoethyl)-3-(phenylmethoxy)-2,5-Pyridine-dicarboxylic acid 5-ethyl ester 2-methyl ester A 10 L round bottom flask (RBF) was charged with 400 g of crude 1-(2,2-dimethoxyethyl)-1,4-dihydro-4-oxo-3-(phenylmethoxy)-2,5-Pyridinedicarboxylic acid 5-ethyl ester 2-methyl ester (0.95 mol, 1.00 eq.) and 1.80 L formic acid. 200 ml sulfuric acid solution (62 wt % in water, 1.91 mol, 2.00 eq.) was added dropwise at room temperature, within 30 min. The resulting mixture was stirred at room temperature for 5 hours, then cooled to 10-15° C. and quenched with 3.5 L water. The mixture was diluted with 2.0 L ethyl acetate and 1.4 L brine. After decantation, the aqueous layer was extracted with ethyl acetate (1×1.4 L). The combined organic extracts were washed with water (3×1.2 L), dried and concentrated to afford 223.0 g of crude 1,4-dihydro-4-oxo-1-(2-oxoethyl)-3-(phenylmethoxy)-2,5-Pyridine-dicarboxylic acid 5-ethyl ester 2-methyl ester (59.7% yield) as orange oil which was used in the next step without further purification.

Preparation of (4R,12aS)-3,4,6,8,12,12a-hexahydro-4-methyl-6,8-dioxo-7-(phenyl-methoxy)-2H-pyridol[1',2':4,5]pyrazino[2,1-b][1,3]oxazine-9-carboxylic acid ethyl ester A 3 L RBF was charged with 223.0 g of crude 1,4-dihydro-4-oxo-1-(2-oxoethyl)-3-(phenylmethoxy)-2,5-Pyridine-dicarboxylic acid 5-ethyl ester 2-methyl ester (0.57 mol, 1.00 eq.), 54 ml methanol and 1.3 L toluene. A solution of 62.6 g (R)-3-amino-butan-1-ol (0.69 mol, 1.21 eq.) in 300 ml toluene was added dropwise at room temperature, within 60 min. 30 min after completion, 152 ml acetic acid were added dropwise and the mixture was stirred at reflux until complete consumption of starting material (approx. 1 h). The mixture was allowed to cool down to room temperature and concentrated under vacuum. The residue was diluted with 900 ml dichloromethane and washed with water (2×850 ml). The organic phase was dried and concentrated to afford 222.0 g crude (4R,12aS)-3,4,6,8,12,12a-hexahydro-4-methyl-6,8-dioxo-7-(phenyl-methoxy)-2H-pyrido[1',2':4,5]pyrazino[2,1-b][1,3]oxazine-9-carboxylic acid ethyl ester (94.5% yield) as orange oil which was used in the next step without further purification.

Preparation of (4R,12aS)-3,4,6,8,12,12a-hexahydro-4-methyl-6,8-dioxo-7-(phenyl-methoxy)-2H-pyrido[1',2':4,5]pyrazino[2,1-b][1,3]oxazine-9-carboxylic acid A 4 L RBF was charged with 222.0 g of crude (4R,12aS)-3,4,6,8,12,12a-hexahydro-4-methyl-6,8-dioxo-7-(phenyl-methoxy)-2H-pyrido[1',2':4,5]pyrazino[2,1-b][1,3]oxazine-9-carboxylic acid ethyl ester (0.54 mol, 1.00 eq.) and 940 ml methanol. The mixture was cooled to 5° C. with an ice-bath. A solution of 56.5 g lithium hydroxide monohydrate (1.35 mmol, 2.50 eq.) in 750 ml water was added dropwise. After completion, the ice-bath was removed and the mixture stirred at room temperature until complete consumption of starting material (approx. 1 h). The mixture was again cooled with an ice-bath, acidified with 850 ml NCl solution (2 N, 1.78 mol, 3.3 eq.) and then allowed to warm up to room temperature. After 72 h stirring, the precipitate was filtered off and washed with 300 ml water. The solid was slurried in 400 ml methanol, collected by filtration, washed with 300 ml methanol and dried at room temperature under vacuum to give 90.2 g (4R,12aS)-3,4,6,8,12,12a-hexahydro-4-methyl-6,8-dioxo-7-(phenyl-methoxy)-2H-Pyrido[1',2':4,5]pyrazino[2,1-b][1,3]oxazine-9-carboxylic acid (43.6% yield) as yellowish solid.

Chemical purity (HPLC/UV, λ=254 nm): 95.8%.
$^1$H NMR (400 MHz, CDCl$_3$, δ ppm): 1.34 (d, 3H, J=7.0 Hz), 1.50 (dd, 1H, J=14.3, 2.2 Hz), 2.0-2.2 (m, 1H), 3.8-4.0 (m, 2H), 4.16 (dd, 1H, J=13.5, 5.7 Hz), 4.28 (dd, 1H, J=13.5, 3.7 Hz), 4.9-5.1 (m, 1H), 5.16 (dd, 1H, J=5.7, 3.7 Hz), 5.3-5.4 (m, 2H), 7.2-7.4 (m, 3H), 7.5-7.7 (m, 2H), 8.34 (s, 1H).

Preparation of (4R,12aS)-N-[(2,4-difluorophenyl)methyl]-3,4,6,8,12,12a-hexahydro-4-methyl-6,8-dioxo-7-(phenyloxy)-2H-Pyrido[1',2':4,5]pyrazino[2,1-b][1,3]oxazine-9-carboxamide (DTG-1): A 3 L round bottom flask was charged with 180.0 g of (4R,12aS)-3,4,6,8,12,12a-hexahydro-4-methyl-6,8-dioxo-7-(phenylmethoxy)-2H-Pyrido[1',2':4,5]pyrazino[2,1-b][1,3]oxazine-9-carboxylic acid (DTG-2) (0.47 mol, 1.00 eq.) and 1.0 L dichloromethane. To this solution, at room temperature, a slurry of 98.6 g N,N'-carbonyldiimidazole (0.61 mol, 1.30 eq.) in 500 ml dichloromethane was added in portions. The mixture was stirred at RT until complete consumption of starting material (approx. 7 h). Then 2,4 difluorobenzyl amine was added dropwise three times, i.e. initially 67.0 g (0.47 mol, 1.00 eq.) in 160 ml dichloromethane, secondly after 15 h stirring at RT another portion of 13.4 g (93.6 mmol, 0.20 eq.) and, finally, after 6 h stirring, 3.80 g 2,4 difluorobenzyl amine (26.6 mmol, 0.05 eq.). After the third portion, the mixture was stirred for another 15 h at RT. The reaction mixture was washed with 10% NCl solution (620 ml), 10% sodium carbonate (400 ml), water (3×675 ml). The organic phase was dried and concentrated under reduced pressure. The residue was crystallized in 800 ml isopropanol, collected by filtration, washed with isopropanol (400 ml) and dried at room temperature under vacuum to give 222.5 g of 4R,12aS)-N-[(2,4-difluorophenypmethyl]-3,4,6,8,12,12a-hexahydro-4-methyl-6,8-dioxo-7-(phenylmethoxy)-2H-Pyrido[1',2':4,5]pyrazino[2,1-b][1,3]oxazine-9-carboxamide (93.3% yield) as off-white solid.

Chemical purity: 96.6% (HPLC, peak area at λ=254 nm).

$^1$H NMR (400 MHz, CDCl$_3$, δ ppm): 1.32 (d, 3H, J=7.0 Hz), 1.49 (dd, 1H, J=13.9, 1.8 Hz), 2.0-2.2 (m, 1H), 3.8-4.0 (m, 2H), 4.09 (dd, 1H, J=13.5, 5.7 Hz), 4.22 (dd, 1H, J=13.3, 3.5 Hz), 4.32 (s, 1H), 4.63 (d, 2H, J=5.9 Hz), 4.9-5.1 (m, 1H), 5.13 (dd, 1H, J=5.5, 3.9 Hz), 5.2-5.3 (m, 2H), 6.7-6.9 (m, 3H), 7.2-7.4 (m, 4H), 7.61 (d, 2H, J=6.7 Hz), 8.36 (br. s., 1H), 10.40 (br. s., 1H).

Preparation of Dolutegravir:

A 2 L round bottom flask was charged with 68.0 g of 4R,12aS)-N-[(2,4-difluorophenypmethyl]-3,4,6,8,12,12a-hexahydro-4-methyl-6,8-dioxo-7-(phenylmethoxy)-2H-Pyrido[1',2':4,5]pyrazino[2,1-b][1,3]oxazine-9-carboxamide (DTG-1) (0.13 mol, 1.00 eq.), 68 ml methanol and 610 ml tetrahydrofuran. The flask was flushed with argon, and 2.40 g 10% palladium on activated charcoal (2.2 mmol, 0.017 eq.) were added. The resulting mixture was stirred at RT, under hydrogen atmosphere, for 15 h. The flask was again flushed with argon, the solid was filtered off and the filtrate was concentrated. Pd/C filter cake was suspended in recovered solvents (600 ml), filtered and the filtrate was concentrated. The combined residues were dissolved in 370 ml absolute ethanol by heating to reflux; the solution was gradually cooled down in air to RT then with an ice-bath. The precipitate was collected by filtration, washed with ethanol (300 ml) and dried at room temperature under vacuum to give 47.6 g of Dolutegravir (85.0% yield) ("Form I") as off-white solid. Chemical purity: 99.7% (HPLC, peak area at λ=254 nm). LC-MS: m/z=420.1, ([M+H—Na]$^+$);

$^1$H NMR (400 MHz, DMSO-d6, δ ppm): 1.31 (d, 3H, J=6.8 Hz), 1.53 (d, 1H, J=13.6 Hz), 1.9-2.1 (m, 1H), 3.88 (d, 1H, J=8.0 Hz), 4.01 (pseudo t, 1H, J=11.8 Hz), 4.33 (dd, 1H, J=13.2, 5.6 Hz), 4.5-4.6 (m, 3H), 4.7-4.8 (m, 1H), 5.43 (s, 1H), 7.04 (pseudo t, 1H, J=8.6 Hz), 7.22 (pseudo t, 1H, J=10.0 Hz), 7.37 (dd, 1H, J=16.0, 8.0 Hz), 8.47 (s, 1H), 10.33 (s, 1H), 12.47 (s, 1H).

IR [cm$^{-1}$]: 3186, 3070, 2979, 2888, 1658, 1628, 1575, 1538, 1498, 1449, 1429, 1415, 1370, 1355, 1310, 1264, 1238, 1207, 1189, 1168, 1132, 1090, 1081, 1066, 1056, 1024, 958, 930, 885, 837, 802, 781, 764, 723, 714, 662, 603.

Example 1

Preparation of Amorphous Dolutegravir Potassium Salt

Crystalline Dolutegravir potassium form II (1.50 g) was dissolved in 30 ml water at 50° C. The mixture was cooled to RT and diluted with 60 ml ethanol. After stirring for 30 min at RT, the mixture was concentrated at 50° C. under reduced pressure and dried at 45° C./30 mbar overnight yielding 1.39 g of amorphous Dolutegravir potassium salt (93% yield) as yellowish solid (Purity 99.4%).

Example 2A

Preparation of Crystalline Dolutegravir Potassium Form II (Reaction with Potassium Ethoxide)

To a slurry of 1.00 g Dolutegravir (free acid) prepared as described above in 20 ml of ethanol, at RT, 0.211 g potassium ethoxide (2.50 mmol, 1.05 eq.) was added portionwise. The resulting mixture was diluted with 20 ml ethanol and heated to 80° C. with stirring. After aging for 5 min at reflux, the mixture was gradually cooled down to RT. The precipitate was collected by filtration, washed with 30 ml ethanol and dried at 45° C./20 mbar overnight to give 1.03 g of Dolutegravir potassium Form II (94% yield) as white solid (Purity 99.5%).

Example 2B

Preparation of Crystalline Dolutegravir Potassium Form II (Reaction with Potassium Ethoxide)

To a slurry of 1.00 g Dolutegravir (free acid) prepared as described above in 20 ml of ethanol, at RT, 0.211 g potassium ethoxide (2.50 mmol, 1.05 eq.) was added portionwise. The resulting mixture was diluted with 20 ml ethanol and heated in an oil bath at 80° C. for 30 minutes with stirring. After aging for 5 min at reflux the mixture was gradually cooled down to RT by removal of the oil bath and allowing to cool (from removal of the oil bath, the mixture was stirred for a total of 90 minutes). The precipitate was collected by filtration, washed with 30 ml ethanol and dried at 45° C./20 mbar overnight to give 1.03 g of Dolutegravir potassium Form II (94% yield) as white solid.

Example 3A

Preparation of Crystalline Dolutegravir Potassium Form II 5.00 g Dolutegravir (free acid) prepared as described above was suspended in 30 ml of ethanol. The stirred mixture was heated to 80° C. and 6.75 ml KOH solution (2 N, 2.62 mmol, 1.10 eq.) was added dropwise within 3 min. The resulting mixture was diluted with 100 ml ethanol then gradually cooled down to RT within 30 min. The precipitate was collected by filtration, washed with 120 ml ethanol and dried at 45° C./20 mbar overnight to give 5.84 g of Dolutegravir potassium Form II (107% yield, calculated based on the molecular weight of anhydrous, non-solvated Dolutegravir potassium) as white solid.

Example 3B

Preparation of Crystalline Dolutegravir Potassium Form II 5.00 g Dolutegravir (free acid) prepared as described above was suspended in 30 ml of ethanol. The stirred mixture was heated to 80° C. in an oil bath and 6.75 ml KOH solution (2 N, 2.62 mmol, 1.10 eq.) was added dropwise during the heating, within a period of 3 min The resulting mixture was diluted with 100 ml ethanol then gradually cooled down to RT within 30 min by removal of the oil bath. The precipitate was collected by filtration (time period between dilution with ethanol and isolation by filtration was 90 minutes), washed with 120 ml ethanol and dried at 45° C./20 mbar overnight to give 5.84 g of Dolutegravir potassium Form II as white solid.

Example 4

Preparation of Crystalline Dolutegravir Potassium Form III

Crystalline Dolutegravir potassium form II (according to example 3A) was dried at 70° C./25 mbar for 24h yielding Dolutegravir potassium form III as white solid (Purity 98.0%).

Example 5

Preparation of Crystalline Dolutegravir Potassium Form IV

Crystalline Dolutegravir potassium form III was left in air at RT for 4 days then stored at 45° C./75% relative humidity for at least 8 days yielding Dolutegravir potassium form IV as off-white solid (Purity 99.1%).

Example 6

Preparation of Crystalline Dolutegravir Potassium Form V

Crystalline Dolutegravir potassium form III was left in air at RT for 4 days then stored at RT/100% relative humidity for 3 days yielding Dolutegravir potassium form V as yellowish solid.

Example 7

Preparation of Crystalline Dolutegravir Potassium Form VI

Crystalline Dolutegravir potassium form III (30.3 g) was suspended in 300 ml water. The mixture was stirred at RT overnight then filtrated and dried at 45° C./20 mbar for 24 h yielding 22.8 g of Dolutegravir potassium form VI (70% yield calculated based on the molecular weight of anhydrous, non-solvated Dolutegravir potassium) as white solid (Purity 99.5%).

Example 8

Preparation of Crystalline Dolutegravir Potassium Form VII

Dolutegravir free-acid crystalline form I (55.00 g) prepared e.g. as described above, was suspended in 366 ml water. The mixture was stirred at RT for 10 min then an aqueous solution of KOH (prepared by dissolving 9.52 g KOH in 66 ml water) was added dropwise. The resulting yellow solution was further stirred at RT for 1.5 h then seeded with 50 mg Dolutegravir potassium form VI. Crystallization started within 5 min. The mixture was further stirred at RT for 1.5 h then cooled with an ice-bath for 2 h. The precipitate was collected by filtration, washed with 150 ml cold water and dried at 45° C./30 mbar overnight to give 50.20 g of Dolutegravir potassium form VII (77% yield, calculated based on the molecular weight of Dolutegravir potassium di-hydrate) as white solid (Purity 99.6%).

Example 9

Determination of the Dissolution

In the following examples, anhydrous Dolutegravir Na as disclosed in WO2010068253 is employed.
1$^{st}$ Experiment:
Approx. 350 mg test substance was weighed into a glass vial, followed by addition of 5 ml solvent. A stirring bar was added, the vial was fixed in a water bath at 37° C. and the suspension was stirred with approx. 500 rpm. After 1 h and 24 h, samples were withdrawn, filtered through a 0.2 μm disposable filter, 50 μl of the clear filtrate were diluted with 950 μl DMSO and 2 μl thereof were analyzed by HPLC/UV.
2$^{nd}$ Experiment:
Approx. 210 mg test substance was weighed into a glass vial, followed by addition of 3 ml solvent. A stirring bar was added, the vial was fixed in a water bath at 37° C. and the suspension was stirred with approx. 250 rpm. After 5, 15 and 60 min, samples were withdrawn, filtered through a 0.2 μm disposable filter, 50 μl of the clear filtrate were diluted with 950 μl DMSO and 2 μl thereof were analyzed by HPLC/UV.
HPLC/UV-Method for Quantification of Dolutegravir
Instrument: Agilent 1200 (G3324)
Method: DOLUTEGRAVIR-SOL-G3324.M
Column: YMC Triart C18, 100*3.0 mm, 3.0μ
Flow: 0.6 ml/min.
Temperature: 40.0° C.
Eluent
A: acetonitrile
B: 0.2% formic acid+0.1% Heptafluorobutyric acid (HFBA)

|  | Time [min] | eluent A [%] | eluent B [%] |
|---|---|---|---|
| Gradient: | 0.0 | 35 | 65 |
|  | 3.2 | 70 | 30 |
|  | 4.0 | 85 | 15 |
|  | 4.5 | 85 | 15 |
|  | 4.7 | 35 | 65 |
|  | 6.5 |  |  |
| Stop time | 8.0 |  |  |

Injection volume: 2 d
Detection: Diode Array Detector (DAD) (λ=258 nm)
A calibration curve was established by linear regression analysis of concentration/peak area data pairs obtained by twofold analysis of a set of calibration solutions containing dolutegravir at concentrations between 10 μg/ml and 1,000 μg/ml. In case that the peak area of dolutegravir in an analyzed sample exceeded the upper limit of the calibration range, the sample was diluted and re-analyzed.
Results of the 1$^{st}$ Experiment:

|  | Concentration [mg/ml] | | | |
|---|---|---|---|---|
|  | Dolutegravir-K (Form VI) | | Dolutegravir-Na | |
| solvent | 1 h | 24 h | 1 h | 24 h |
| 0.1M HCl pH1.2 | 20.35 | 20.27 | 0.084 | 0.412 |
| 20 mM Sodium acetate (NaAc) pH 4.5 | 21.77 | 16.93 | 0.595 | 0.634 |
| 50 mM KH$_2$PO$_4$ pH 6.8 | 32.58 | 33.44 | 0.894 | 0.918 |

Results of the 2$^{nd}$ Experiment:

Solvent: 0.1 N HCl

| sample | concentration [mg/ml] | | |
|---|---|---|---|
| | 5 min | 15 min | 60 min |
| Dolutegravir-Na (anhydrous) | 0.33 | 0.42 | 0.40 |
| Dolutegravir-K (Form VII) | 0.08 | 23.78 | 25.93 |
| Dolutegravir-K (amorphous) | 0.30 | 21.26 | 15.40 |

Solvent: 50 mM KH$_2$PO$_4$, pH 6.8

| | concentration [mg/ml] | | |
|---|---|---|---|
| | 5 min | 15 min | 60 min |
| Dolutegravir-Na | 0.27 | 1.19 | 1.24 |
| Dolutegravir-K (Form VII) | 22.0 | 23.9 | 23.3 |
| Dolutegravir-K (amorphous) | 39.1 | 40.9 | 60.1 |

Solvent: Demineralized Water

| | concentration [mg/ml] | | |
|---|---|---|---|
| | 5 min. | 15 min. | 60 min. |
| Dolutegravir-Na | 3.30 | 3.43 | 3.50 |
| Dolutegravir-K (Form VII) | 39.5 | 44.0 | 44.1 |
| Dolutegravir-K (amorphous) | 55.6 | 55.1 | 62.3 |

Example 10

Preparation of a Pharmaceutical Composition Comprising Dolutegravir Potassium Salt Tablets were prepared using the ingredients as summarized in the following table 1:

TABLE 1

| Compound | Brand ® | amount [mg] | amount [%] |
|---|---|---|---|
| Intragranular phase | | | |
| Dolutegravir potassium | — | 56.43* | 23.51 |
| HPMC | Pharmacoat 603 | 8.00 | 3.33 |
| Sodium lauryl sulphate (SLS) | — | 2.00 | 0.83 |
| Lactose monohydrate | Granulac 200 | 60.00 | 25.00 |
| Microcrystalline cellulose | Avicel PH 101 | 50.00 | 20.83 |
| Croscarmellose sodium | Ac-Di-Sol | 5.00 | 2.08 |
| Extra granular phase | | | |
| Magnesium stearate | — | 2.90 | 1.21 |
| Croscarmellose sodium | Ac-Di-Sol | 5.00 | 2.08 |
| Silicified Microcrystalline cellulose | Prosolv SMCC 90 | 50.67 | 21.11 |
| TOTAL | | 240.00 | 100.00 |

*adapted to the potency of Dolutegravir potassium

Manufacturing Description

An aqueous solution comprising Pharmacoat 603 was prepared. Agitation was required in order to achieve complete solution. Dolutegravir potassium, SLS, Granulac 200, Ac-di-Sol and Avicel PH 101 were granulated with the before prepared solution. The obtained granules were sieved through 200 μm mesh size and subsequently dried at 40° C. After sieving the dried granules through 630 μm mesh size Prosolv SMCC 90 and Ac-Di-Sol were added. The mixture was blended for 10 minutes in a Turbula T10B tumble mixer. After addition of magnesium stearate blending was continued for further 3 minutes. Finally, the blend was compressed into tablets on an eccentric press (e.g. Korsch Ek0) with a 9 mm tablet punch.

The dissolution profile of the above potassium salt formulation in 900 ml of 0.1 N HCl, paddle (no sinker) at 100 rpm, 37° C. was tested. The dissolution is presented in FIG. 24.

Example 11

Preparation of a Pharmaceutical Composition Comprising Dolutegravir Sodium Salt

Tablets were prepared using the ingredients as summarized in table 2:

TABLE 2

| Compound | Brand ® | amount [mg] | amount [%] |
|---|---|---|---|
| Intragranular phase | | | |
| Dolutegravir sodium | — | 53.24* | 22.18 |
| HPMC | Pharmacoat 603 | 8.00 | 3.33 |
| Sodium lauryl sulphate (SLS) | — | 2.00 | 0.83 |
| Lactose monohydrate | Granulac 200 | 60.00 | 25.00 |
| Microcrystalline cellulose | Avicel PH 101 | 49.76 | 20.73 |
| Croscarmellose sodium | Ac-Di-Sol | 5.00 | 2.08 |
| Extra granular phase | | | |
| Magnesium stearate | — | 2.90 | 1.21 |
| Silicified MCC | Prosolv SMCC 90 | 54.10 | 22.54 |
| Croscarmellose sodium | Ac-Di-Sol | 5.00 | 2.08 |
| TOTAL | | 240.00 | 100.00 |

*adapted to the potency of Dolutegravir sodium

Manufacturing Description

An aqueous solution comprising Pharmacoat 603 was prepared. The active, Granulac 200, SDS, Avicel PH 101 and Ac-Di-Sol were granulated with the before prepared solution. The obtained granules were sieved through 1650 μm mesh size and subsequently dried at 40° C. After sieving the dried granules through 630 μm mesh size, Prosolv and Ac-Di-Sol were added. The mixture was blended for 10 minutes in a Turbula T10B tumble mixer. After addition of Magnesium stearate, blending was continued for 3 minutes. Finally, the blend was compressed into tablets on an eccentric press Ek0 with a 9 mm tablet punch. The dissolution profile of the above sodium salt formulation in 900 ml of 0.1 N HCl, paddle (no sinker) at 100 rpm, 37° C. was tested. The dissolution is presented in FIG. 24.

The invention claimed is:
1. A Dolutegravir potassium salt.
2. The Dolutegravir potassium salt according to claim 1 wherein the Dolutegravir potassium salt is in crystalline or amorphous form.

3. The Dolutegravir potassium salt according to claim 2, wherein the Dolutegravir potassium salt is in a crystalline form selected from:
   a) crystalline Form VII of Dolutegravir potassium, characterized by data selected from one or more of the following: a PXRD pattern having peaks at 6.5, 9.2, 10.4, 21.6 and 26.6 degrees 2-theta±0.2 degrees 2-theta; a PXRD pattern as depicted in FIG. 19; and combinations of these data; or
   b) crystalline Form VI of Dolutegravir potassium, characterized by data selected from one or more of the following: a PXRD pattern having peaks at 8.6, 12.0, 14.3, 19.2 and 26.0 degrees 2-theta±0.2 degrees 2-theta; a PXRD pattern as depicted in FIG. 12; and combinations of these data.

4. The Dolutegravir potassium salt according to claim 3 that is in said crystalline Form VII, characterized by data selected from one or more of the following: a PXRD pattern having peaks at 6.5, 9.2, 10.4, 21.6 and 26.6 degrees 2-theta±0.2 degrees 2-theta; a PXRD pattern as depicted in FIG. 19; and combinations of these data.

5. The Dolutegravir potassium salt according to claim 3 that is in said crystalline Form VII, characterized by a PXRD pattern having peaks at 6.5, 9.2, 10.4, 21.6 and 26.6 degrees 2-theta±0.2 degrees 2-theta.

6. The Dolutegravir potassium salt according to claim 5, further characterized by any one, two, three, four, five, six or seven peaks selected from 7.4, 14.1, 17.5, 24.5 and 27.9 degrees 2-theta±0.2 degrees 2-theta.

7. The Dolutegravir potassium salt according to claim 5, further characterized by an absence of one, two, three, four or five XPRD peaks selected from 4.8, 6.0, 6.9, 8.6 and 12.0 degrees 2-theta±0.2 degrees 2-theta.

8. The Dolutegravir potassium salt according to claim 5, further characterized by a DSC thermogram showing a very broad endotherm between about 40° C. to about 140° C. (±2° C.), a very small exotherm between 260° C. and 267° C. (±2° C.), an endotherm with an onset temperature at about 327.5° C. (±0.5° C.) and a peak temperature of about 331.9° C. (±0.5° C.), followed by a broad exotherm, which corresponds to decomposition of the sample.

9. The Dolutegravir potassium salt according to claim 3 that is in said crystalline Form VII, further characterized by data selected from one or more of the following: a DSC thermogram as depicted in FIG. 20; a TGA thermogram as depicted in FIG. 21; an FTIR spectrum as depicted in FIG. 22; and combinations of these data.

10. The Dolutegravir potassium salt according to claim 3 that is in said crystalline Form VII, wherein said form is a dihydrate.

11. The Dolutegravir potassium salt according to claim 3 that is in said crystalline Form VI, characterized by data selected from one or more of the following: a PXRD pattern having peaks at 8.6, 12.0, 14.3, 19.2 and 26.0 degrees 2-theta±0.2 degrees 2-theta; a PXRD pattern as depicted in FIG. 12; and combinations of these data.

12. The Dolutegravir potassium salt according to claim 3 that is in said crystalline Form VI, characterized by a PXRD pattern having peaks at 8.6, 12.0, 14.3, 19.2 and 26.0 degrees 2-theta±0.2 degrees 2-theta.

13. The Dolutegravir potassium salt according to claim 12, further characterized by any one, two, three, four or five peaks selected from 7.4, 14.8, 23.6, 27.0 and 31.3 degrees 2-theta±0.2 degrees 2-theta.

14. The Dolutegravir potassium salt according to claim 12, further characterized by a DSC thermogram showing a very broad endotherm between about 40° C. to about 145° C. (±2° C.), a very small exotherm between 259° C. and 266° C. (±2° C.), an endotherm with an onset temperature at about 326.5° C. (±0.5° C.) and a peak temperature of about 332.4° C. (±0.5° C.), followed by a broad exotherm, which corresponds to decomposition of the sample.

15. The Dolutegravir potassium salt according to claim 11, further characterized by a DSC thermogram as depicted in FIG. 13; a TGA thermogram as depicted in FIG. 14; an FTIR spectrum as depicted in FIG. 18; and combinations of these data.

16. The Dolutegravir potassium salt according to claim 11, wherein said form is a monohydrate.

17. The Dolutegravir potassium salt according to claim 2 that is in said amorphous form, characterized by an X-ray powder diffraction pattern as depicted in FIG. 2.

18. The Dolutegravir potassium salt according to claim 17, characterized by a DSC thermogram showing a very broad endotherm between about 40° C. to about 130° C. (±2° C.), a very small exotherm between 250° C. and 257° C. (±2° C.), a broad endotherm between 290° C. and 330° C. (±2° C.), followed by a broad exotherm, which corresponds to decomposition of the sample.

19. The Dolutegravir potassium salt according to claim 17, further characterized by an FTIR spectrum as depicted in FIG. 3; a DSC thermogram as depicted in FIG. 23, or combinations of these data.

20. A process for preparing Dolutegravir free acid and solid state forms thereof comprising preparing Dolutegravir potassium salt as defined in claim 1 and/or a solid state form thereof, and converting it to Dolutegravir free acid.

21. The process according to claim 20, further comprising the following step:
   acidifying the Dolutegravir potassium salt and/or any solid state form thereof to obtain Dolutegravir free acid.

22. A process for preparing Dolutegravir salts and solid state forms thereof comprising preparing Dolutegravir potassium salt as defined in claim 1 and/or a solid state form thereof, and converting it to a different salt of Dolutegravir.

23. The process according to claim 22, further comprising the following step:
   acidifying the Dolutegravir potassium salt and/or any solid state form thereof to obtain Dolutegravir free acid, and reacting the obtained Dolutegravir free acid with an appropriate base, to obtain the corresponding salt.

24. A pharmaceutical composition comprising Dolutegravir potassium salt as defined in claim 1.

25. A pharmaceutical formulation comprising Dolutegravir potassium salt as defined in claim 1 or a solid state form thereof and at least one pharmaceutically acceptable excipient.

26. A process for preparing the pharmaceutical formulation according to claim 25 comprising combining the Dolutegravir potassium salt or a solid state form thereof, or a mixture thereof, or a pharmaceutical composition comprising Dolutegravir potassium salt or a solid state form thereof, with at least one pharmaceutically acceptable excipient.

27. A method of treating an HIV infection, comprising administering, to a subject suffering from HIV infection or otherwise in need of the treatment, a therapeutically effective amount of the Dolutegravir potassium salt or a solid state form thereof as defined in claim 1.

28. A method of treating an HIV infection, comprising administering, to a subject suffering from HIV infection or otherwise in need of the treatment, a therapeutically effective amount of the pharmaceutical composition as defined in claim 24.

29. A method of treating an HIV infection, comprising administering, to a subject suffering from HIV infection or otherwise in need of the treatment, a therapeutically effective amount of the pharmaceutical composition as defined in claim 25.

30. A pharmaceutical composition comprising Dolutegravir potassium salt as defined in claim 2.

* * * * *